United States Patent [19]

Klemarczyk et al.

[11] 4,324,912
[45] Apr. 13, 1982

[54] CARBOAMIDOALKYL NORBORNANES, ORGANOLEPTIC USES THEREOF AND PROCESS FOR PREPARING SAME

[75] Inventors: Philip T. Klemarczyk, Old Bridge; Frederick L. Schmitt, Holmdel; Edward J. Granda, Englishtown; Domenick Luccarelli, Jr., Ocean, all of N.J.

[73] Assignee: International Flavors & Fragrances Inc., New York, N.Y.

[21] Appl. No.: 206,632

[22] Filed: Nov. 13, 1980

Related U.S. Application Data

[63] Continuation-in-part of Ser. No. 152,188, Jul. 17, 1980, abandoned.

[51] Int. Cl.³ .......................................... C07C 103/19
[52] U.S. Cl. .................................. 564/188; 564/76; 252/522 R; 424/76; 424/54
[58] Field of Search .......................................... 564/188

[56] References Cited

U.S. PATENT DOCUMENTS

| | | | |
|---|---|---|---|
| 2,872,483 | 2/1959 | Bloch | 564/188 |
| 3,758,599 | 9/1973 | Lorette | 585/252 |
| 4,087,551 | 5/1978 | May | 564/188 X |
| 4,150,052 | 4/1979 | Watson et al. | 564/123 |
| 4,193,936 | 3/1981 | Watson et al. | 564/123 |

FOREIGN PATENT DOCUMENTS 220061  5/1958  Australia .................. 564/188

OTHER PUBLICATIONS

Mellor et al., J. Chem. Soc. Perkin Trans II, 1974 (I) 26–31.

*Primary Examiner*—Charles F. Warren
*Attorney, Agent, or Firm*—Arthur L. Liberman

[57] ABSTRACT

Described are compounds having the generic structure:

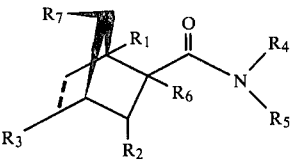

wherein the dashed line represents a carbon-carbon single bond or a carbon-carbon double bond and wherein $R_2$ is methyl or hydrogen; $R_6$ is methyl or hydrogen; $R_1$, $R_3$ or $R_7$ represent methyl or hydrogen, with the proviso that one of $R_1$, $R_3$ and $R_7$ represents methyl and the other two of $R_1$, $R_3$ and $R_7$ represent hydrogen; wherein $R_4$ and $R_5$ are the same or different and each represents hydrogen or $C_1$–$C_3$ lower alkyl. In addition, organoleptic uses of such compounds are disclosed for augmenting or enhancing the aroma or taste of consumable materials including foodstuffs, chewing gums, toothpastes, medicinal products, chewing tobaccos, smoking tobaccos, smoking tobacco articles, perfumes, perfumed articles (such as liquid or solid anionic, cationic, nonionic or zwitterionic detergents, fabric softeners, dryer-added fabric softener articles, fabric brighteners and other perfumed articles and colognes). Also disclosed is a process for preparing such compounds according to the reaction scheme:

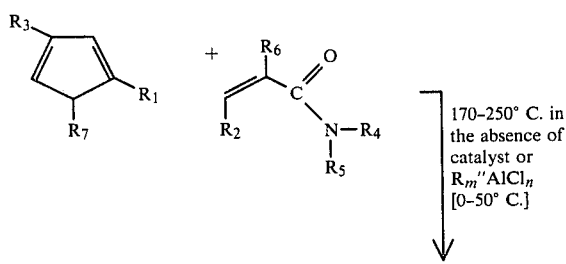

170–250° C. in the absence of catalyst or $R_m'''AlCl_n$ [0–50° C.]

4,324,912
Page 2
-continued
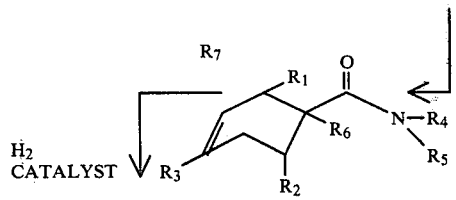
-continued
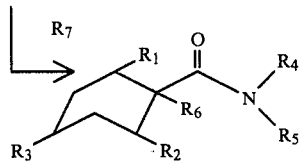
wherein R" represents $C_1$–$C_3$ alkyl; $m+n=3$ with the further proviso that m is 1 or 2 and n is 1 or 2; and wherein $R_1$, $R_2$, $R_3$, $R_4$, $R_5$, $R_6$ and $R_7$ are as defined above.
2 Claims, 18 Drawing Figures

GLC PROFILE FOR EXAMPLE I.

MASS SPECTRUM FOR EXAMPLE I.

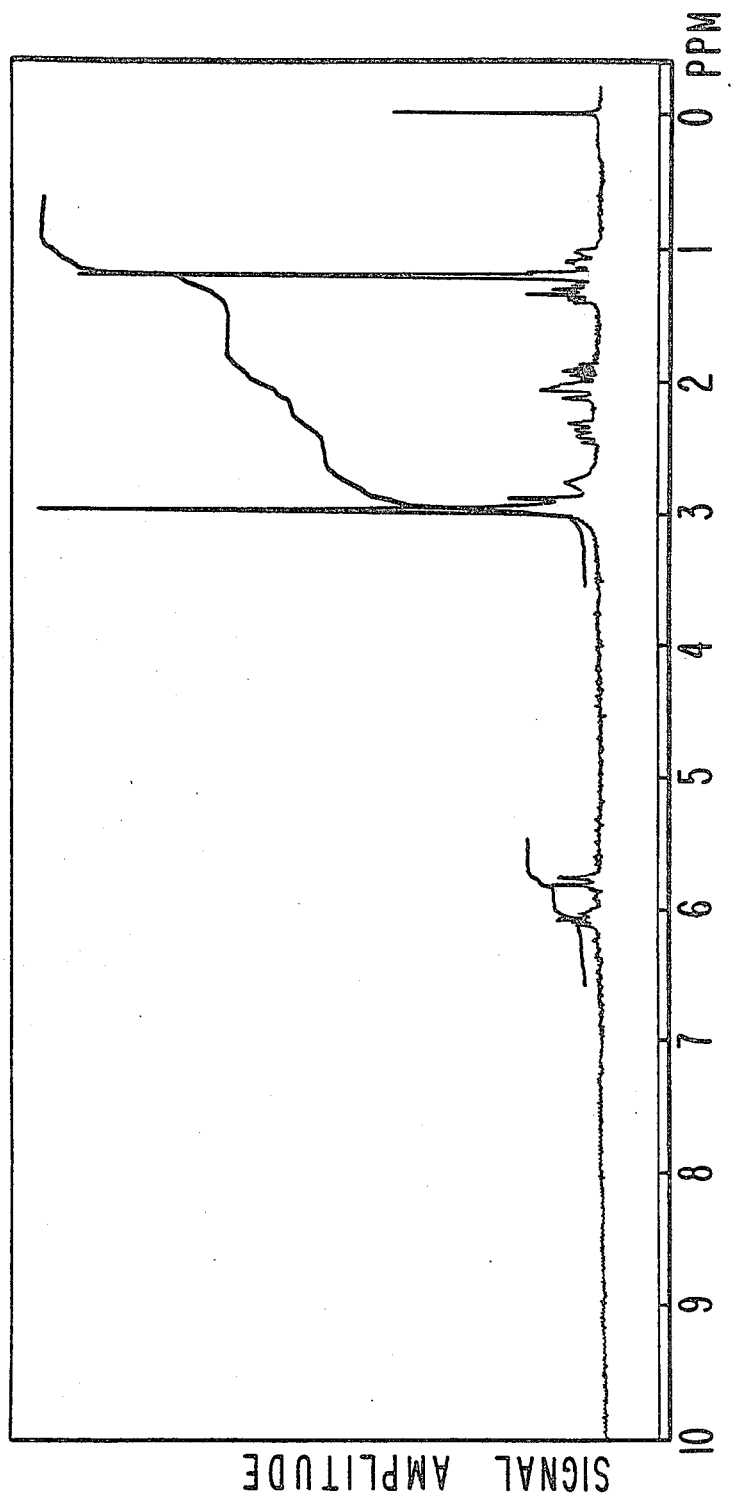

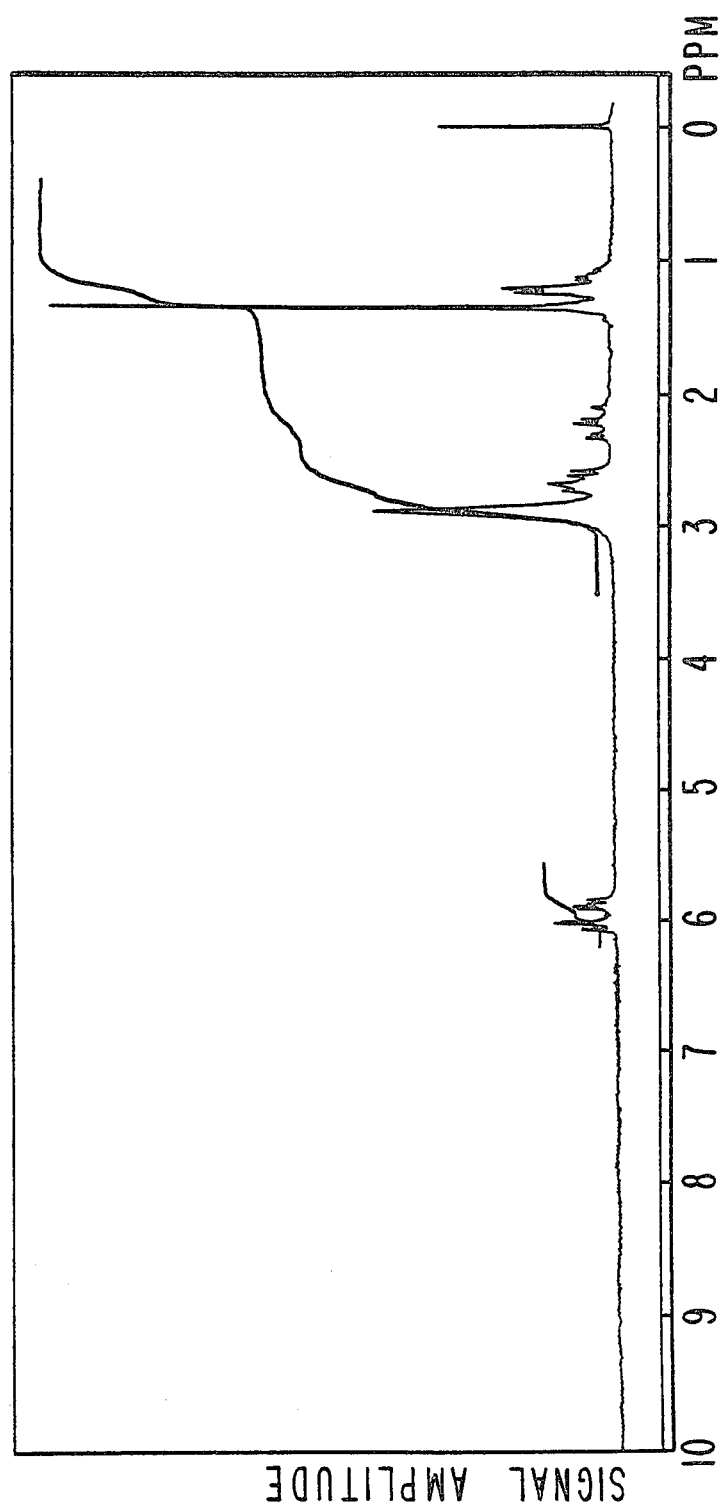

NMR SPECTRUM FOR PEAK 3 OF EXAMPLE I.

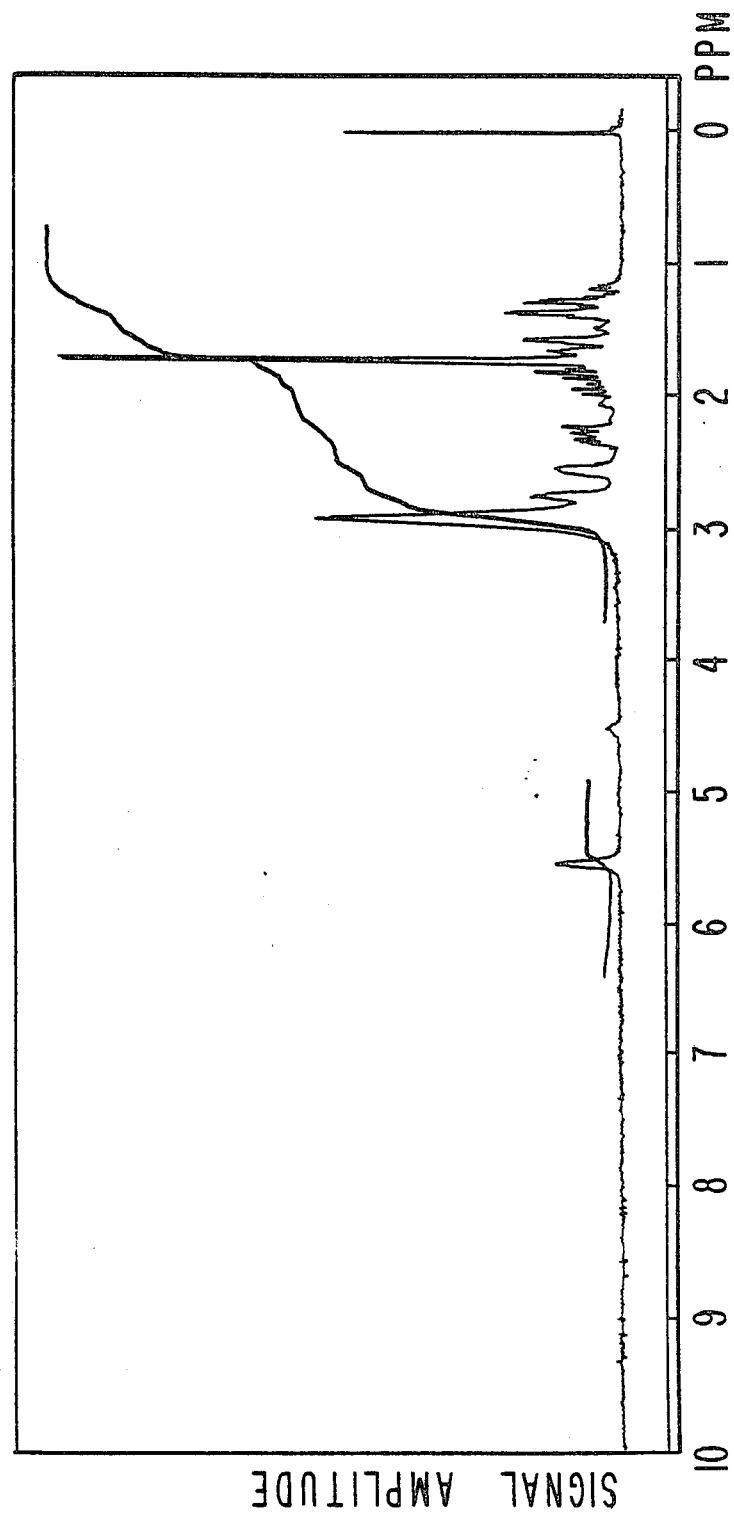

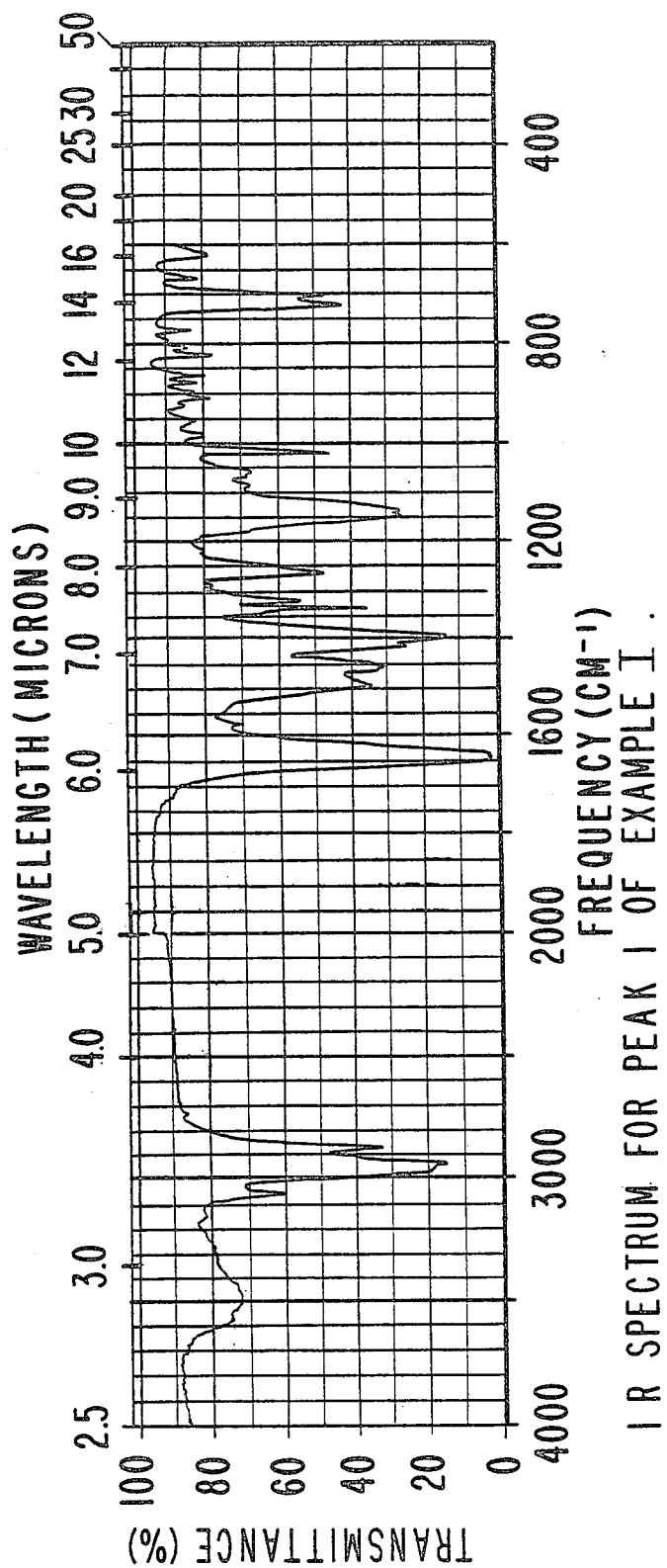

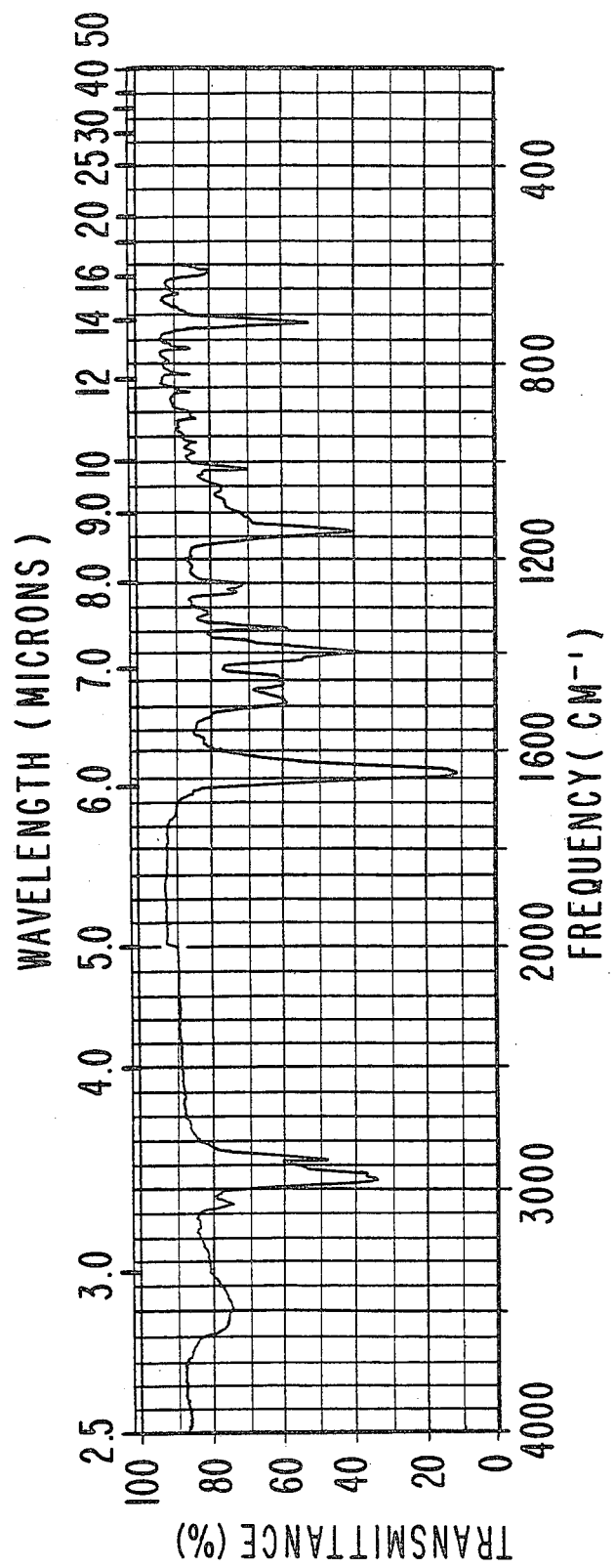

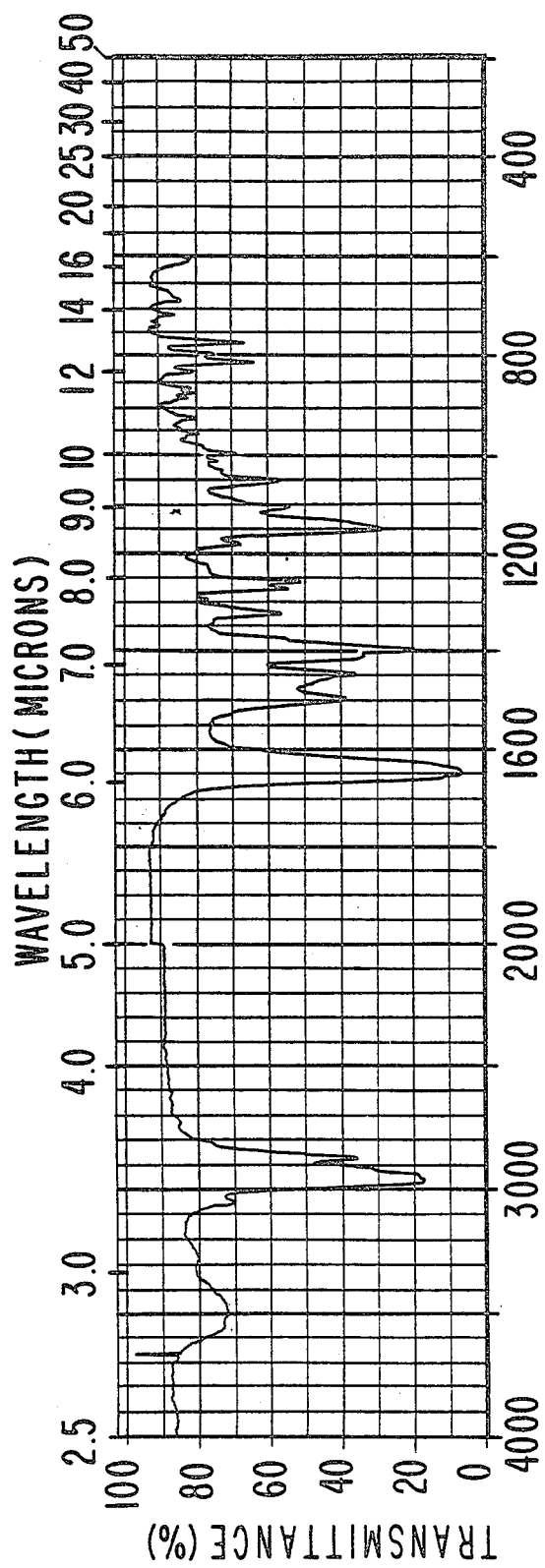

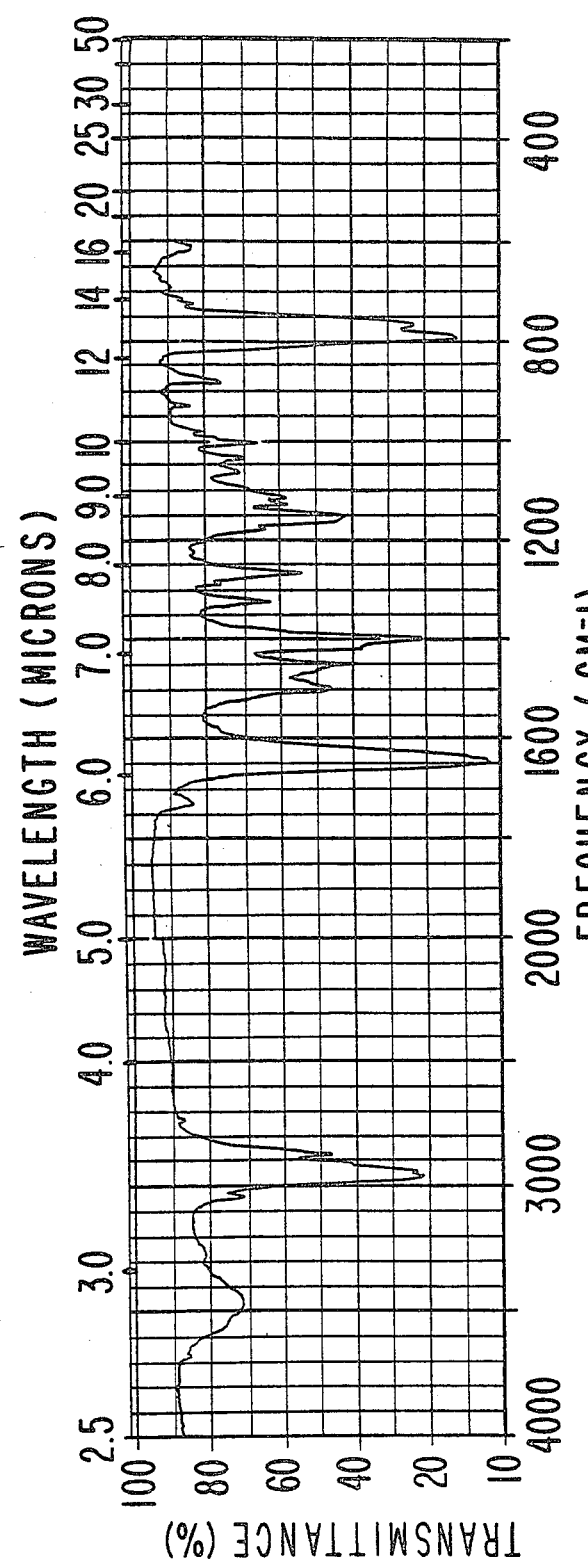

MASS SPECTRUM FOR EXAMPLE II

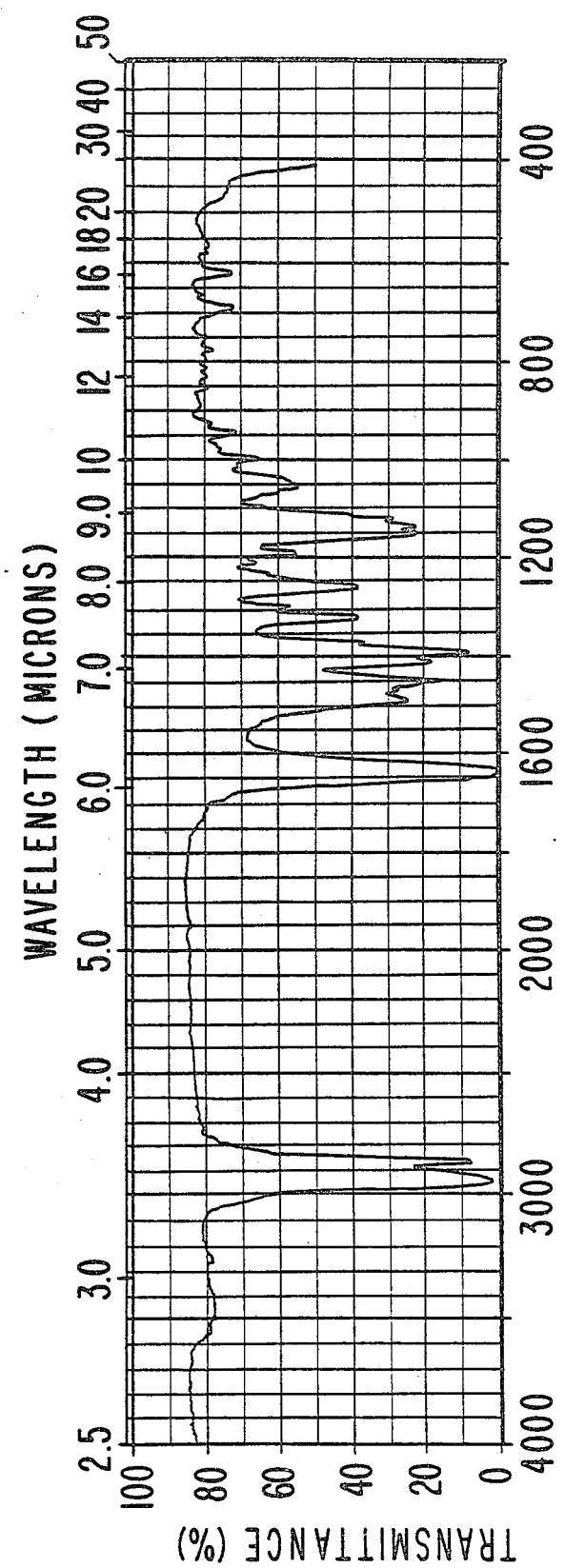

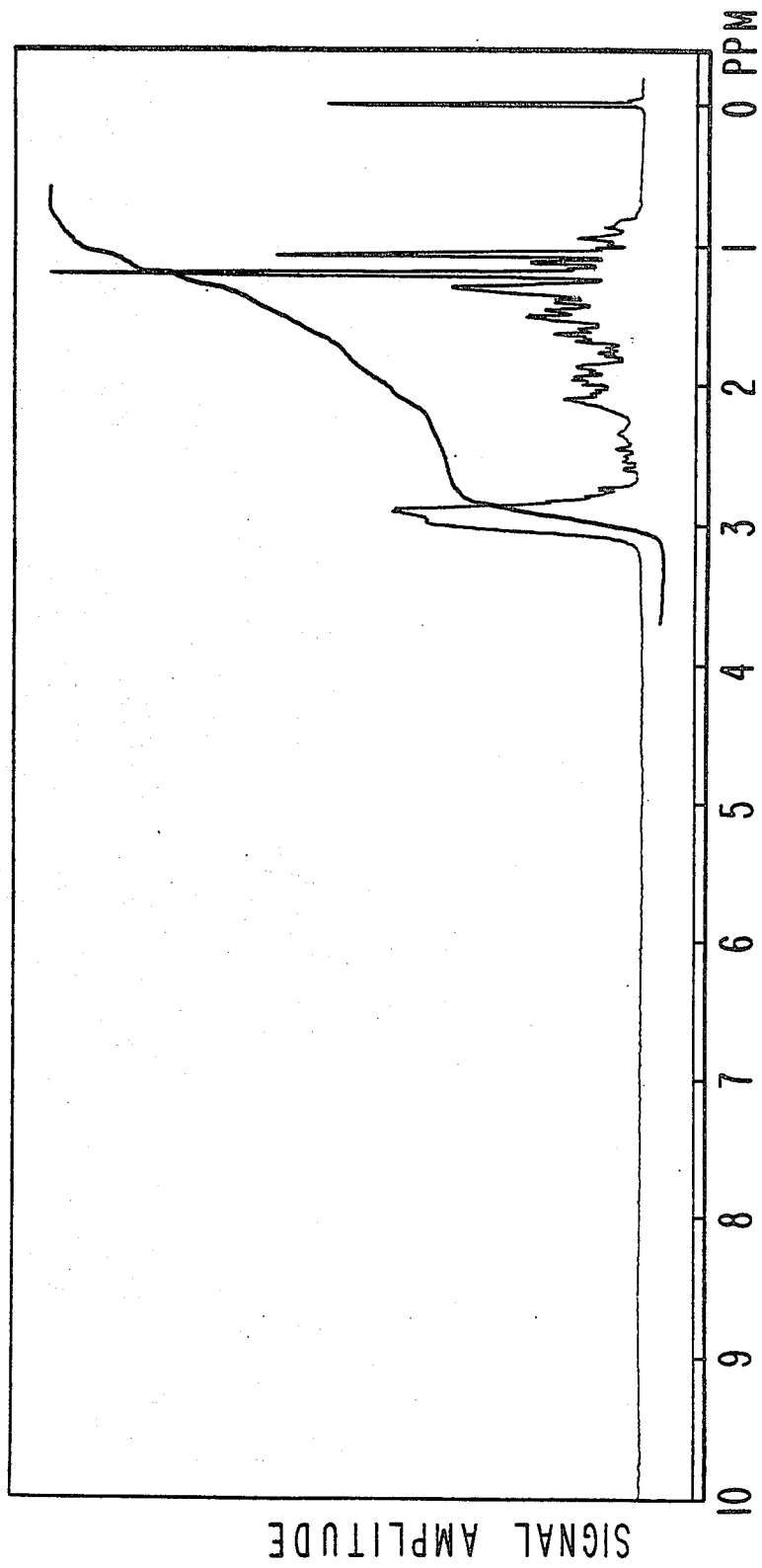

IR SPECTRUM FOR FRACTION 8 OF EXAMPLE II.

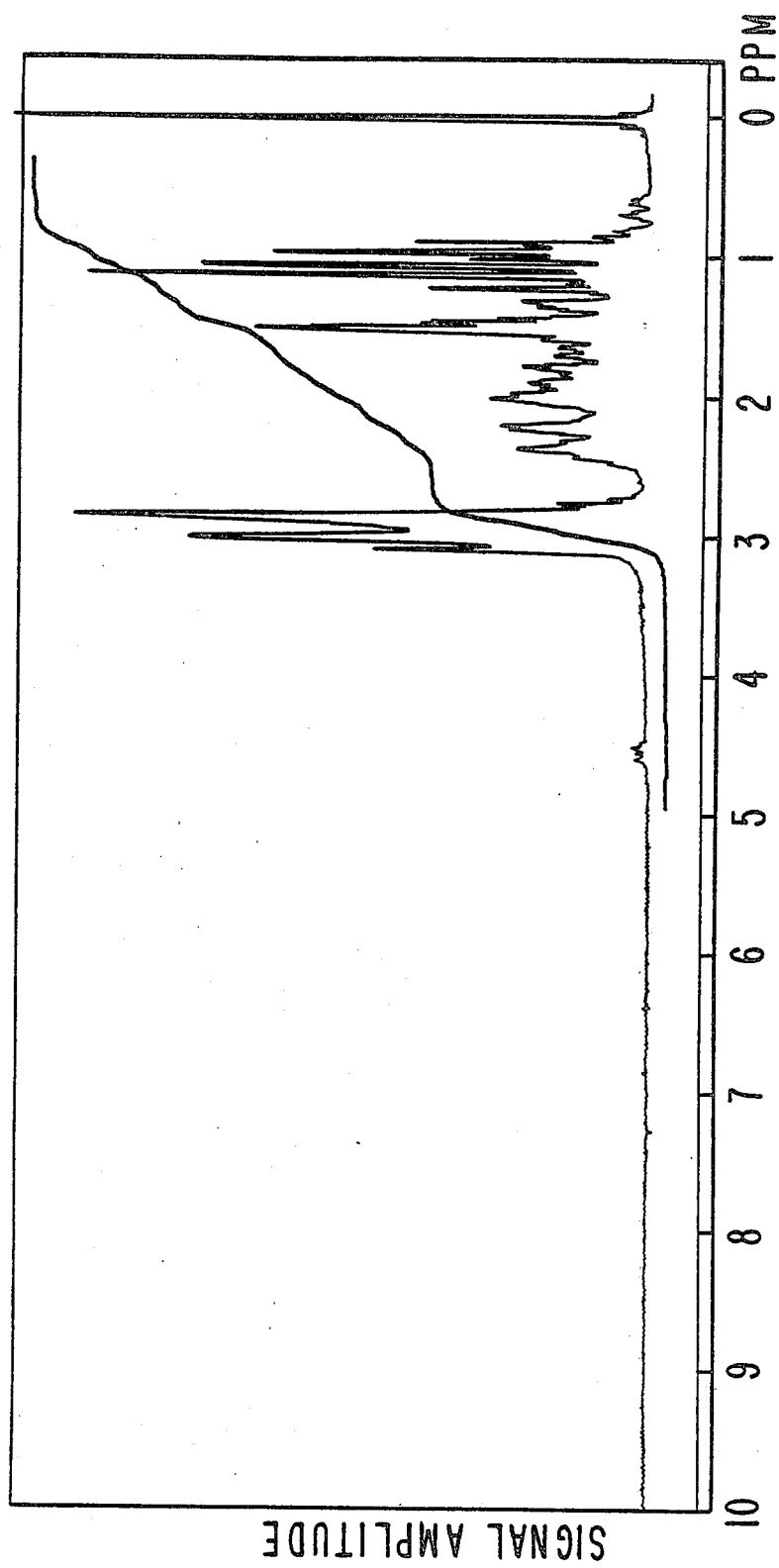

GLC PROFILE FOR EXAMPLE XIX.

NMR SPECTRUM FOR EXAMPLE XIX

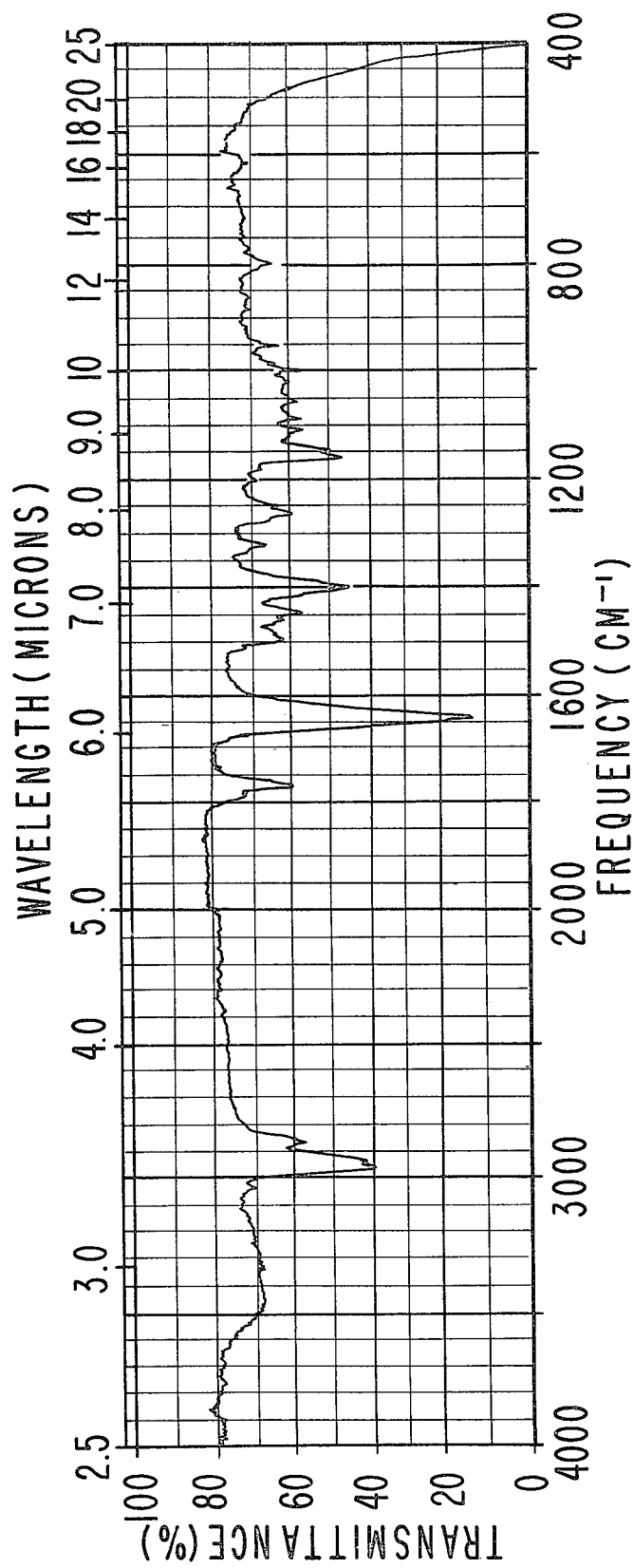

CARBOAMIDOALKYL NORBORNANES, ORGANOLEPTIC USES THEREOF AND PROCESS FOR PREPARING SAME

This application is a continuation-in-part of application for U.S. Letters Patent Ser. No. 152,188 filed on July 17, 1980 now abandoned.

BACKGROUND OF THE INVENTION

The present invention relates to carboamidoalkyl norbornanes having the generic structure:

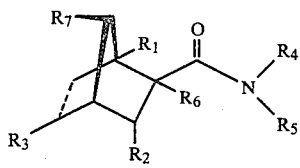

wherein the dashed line represents a carbon-carbon single bond or a carbon-carbon double bond and wherein $R_2$ is methyl or hydrogen; $R_6$ is methyl or hydrogen; $R_1$, $R_3$ or $R_7$ represent methyl or hydrogen, with the proviso that one of $R_1$, $R_3$ and $R_7$ represents methyl and the other two of $R_1$, $R_3$ and $R_7$ represent hydrogen; wherein $R_4$ and $R_5$ are the same or different and each represents hydrogen or $C_1$-$C_3$ lower alkyl, produced by the novel process of our invention and the novel compositions using one or more of such norbornane derivatives to alter, modify or enhance the aroma of certain consumable materials including perfumes, perfumed articles, colognes, foodstuffs, chewing gums, toothpastes, medicinal products, chewing tobaccos, smoking tobaccos and smoking tobacco articles.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Sweet, anise, grapefruit-like and green aroma and taste characteristics are desirable in several types of foodstuffs, chewing gums, medicinal products, toothpastes and chewing tobaccos.

Sweet and fruity aroma and taste nuances are desirable for augmenting or enhancing the aroma and taste of smoking tobaccos, smoking tobacco articles and smoking tobacco flavors.

Herbaceous, spearmint, spicy, caraway, basil, powdery, fruity, castoreum-like and anise aroma characteristics are desirable in several types of perfume compositions, perfumed articles and colognes.

Arctander, "Perfume and Flavor Chemicals", 1969, Volume I discloses the use in perfume compositions and in foodstuff flavors of camphene carbinyl acetate thus:

"1029: 2,2-Dimethyl-Delta-2-betanorbornane-2-ethylacetate "Camphene carbinyl acetate".

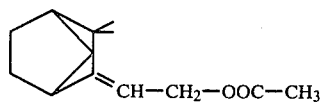

Mild and sweet-woody odor with a floral-piney undertone. The commercial products are probably not well defined single chemicals, and great variations in odor have been observed.

This ester has been developed in line with the research on Sandalwood type odors. The parent alcohol "Camphene carbinol" was once considered useful as a Sandalwood type material, but it has found more use as a sweetening and enriching ingredient in sophisticated Pine fragrances. The title ester finds limited use in perfume compositions of woody character, Fougeres, Pine fragrances, etc. and it blends very well with the Cyclohexanol derivatives, Ionones, iso-Bornylacetate, Nitromusks, etc."

Mellor and Webb, J. Chem. Soc. Perkin Trans II, 1974 (I) 26–31 discloses production of the compounds having the structures:

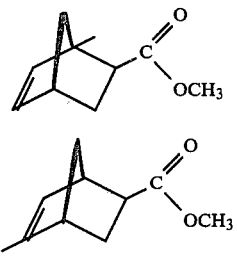

together with several other methyl substituted isomers thereof in admixture, according to the reaction:

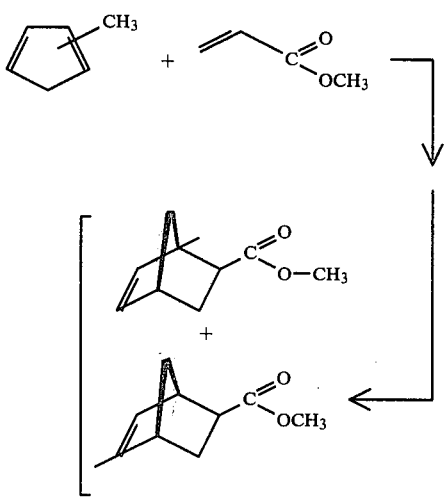

The Mellor and Webb article, however, does not disclose the reaction to take place at low temperatures in the presence of an alkyl aluminum halide or dialkyl aluminum halide whereby but two isomers are produced in a controlled fashion in high yields. Furthermore, the Mellor and Webb article does not disclose the production of carboamido compounds but is merely limited to carboalkoxy compounds.

Thus, nothing in the prior art indicates production for organoleptic uses of compounds having the generic structure:

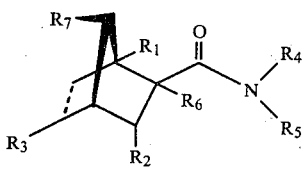

wherein the dashed line represents a carbon-carbon single bond or a carbon-carbon double bond and wherein $R_2$ is methyl or hydrogen; $R_6$ is methyl or hydrogen; $R_1$, $R_3$ or $R_7$ represent methyl or hydrogen, with the proviso that one of $R_1$, $R_3$ and $R_7$ represents methyl and the other two of $R_1$, $R_3$ and $R_7$ represent hydrogen; wherein $R_4$ and $R_5$ are the same or different and each represents hydrogen or $C_1$–$C_3$ lower alkyl.

Belgian Pat. No. 731,124 discloses the butyramide having the structure:

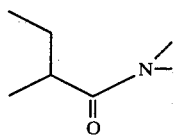

for use in perfumery. It is indicated that this butyramide has a minty aroma and taste. The compound having the structure:

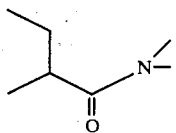

is different in kind, both insofar as structure is concerned and insofar as organoleptic properties are concerned from the compounds of the instant invention.

Belgian Pat. No. 788,461 discloses the use in perfumery of N-phenyl-N-methyl-2-ethyl butyric acid amide which has the structure:

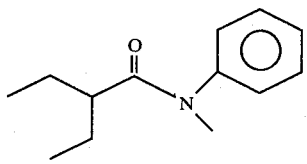

It is indicated that this material has an herbaceous scent with a grapefruit-like note, being useful in perfumes, cosmetic products, foodstuffs and drinks. The structure of the compound of Belgian Pat. No. 788,461 is different in kind from the structure of the compounds of the instant case, and furthermore, the organoleptic properties of the compound of Belgian Pat. No. 788,461 are different in kind from the organoleptic properties of the compounds of the instant case.

U.S. Pat. No. 4,193,936 issued on Mar. 18, 1980 (division of Ser. No. 796,973, filed on May 16, 1977, now U.S. Pat. No. 4,150,052) discloses substantially odorless non-volatile, physiologically active cooling compositions having the formula:

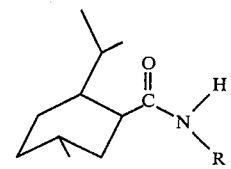

wherein R is $C_1$–$C_9$ alkyl, $C_3$–$C_7$ cycloalkyl or a substituted phenyl radical of up to ten carbon atoms, containing as substituents one or more groups selected from $C_1$–$C_4$ alkyl, hydroxy, $C_1$–$C_4$ alkoxy, nitro and halogen. The compounds of U.S. Pat. No. 4,193,936 as well as those of U.S. Pat. No. 4,150,052, are different in kind from the compounds of our invention, and furthermore, their organoleptic properties are different in kind from the organoleptic properties of the compounds of our invention.

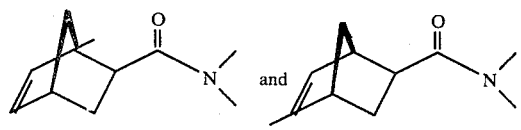

Figure 2:
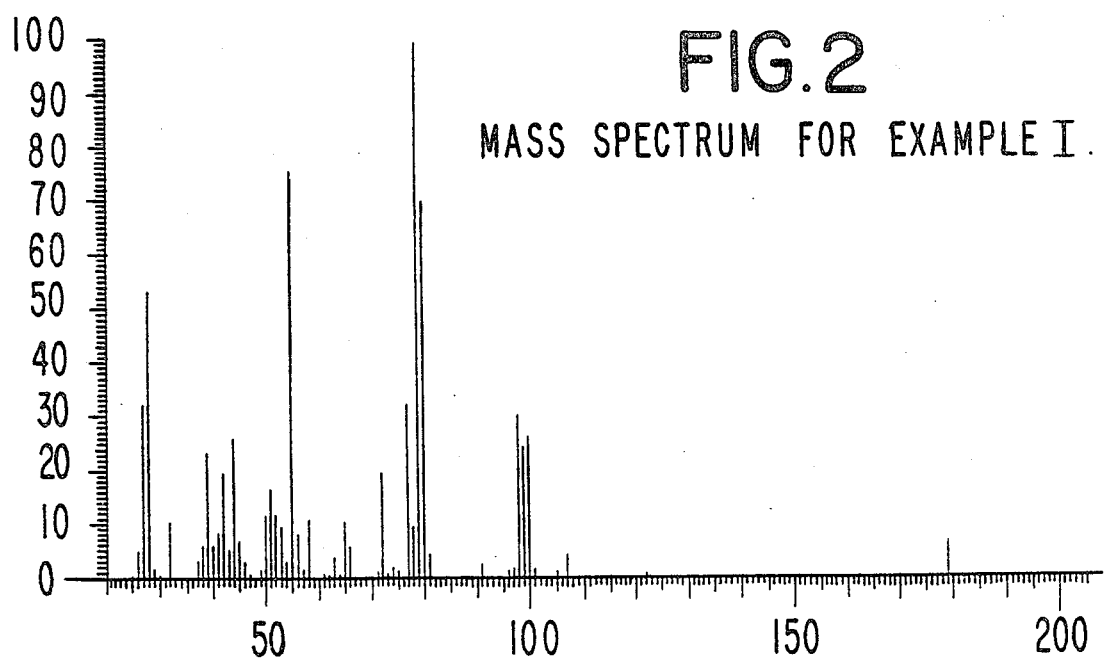

FIG. 2 represents the mass spectrum for the reaction product of Example I which contains the compounds having the structures:

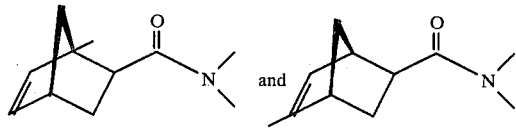

FIG. 3A represents the NMR spectrum for peak 1 of the GLC profile of the reaction product of Example I which represents the compound having the structure:

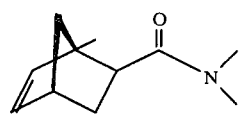

FIG. 3B represents the NMR spectrum for peak 2 of the GLC profile of the reaction product of Example I which represents the compound having the structure

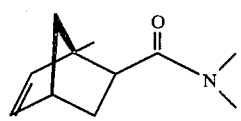

Figure 3C:
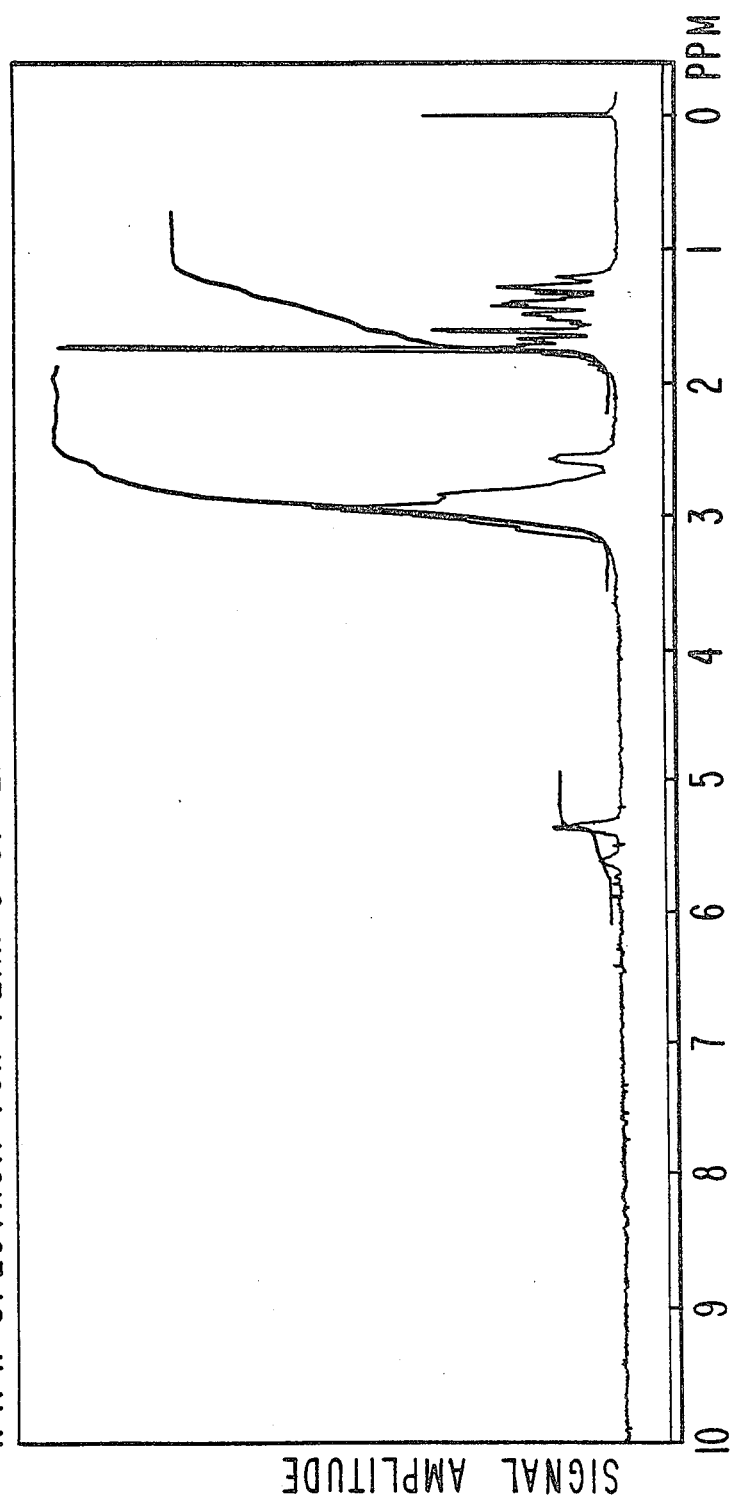

FIG. 3C represents the NMR spectrum for peak 3 of the GLC profile of the reaction product of Example I and represents the compound having the structure:

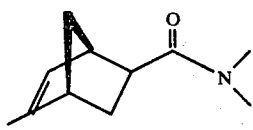

FIG. 3D represents the NMR spectrum for peak 4 of the GLC profile of the reaction product of Example I and represents the compound having the structure:

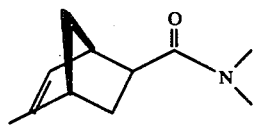

FIG. 4A represents the infra-red spectrum for peak 1 of the GLC profile of the reaction product of Example I which represents the compound having the structure:

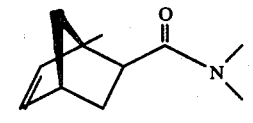

FIG. 4B represents the infra-red spectrum for peak 2 of the GLC profile of the reaction product of Example I and represents the compound having the structure:

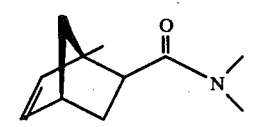

FIG. 4C represents the infra-red spectrum for peak 3 of the GLC profile of the reaction product of Example I and represents the compound having the structure:

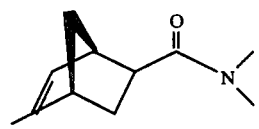

FIG. 4D represents the infra-red spectrum for peak 4 of the GLC profile of the reaction product of Example I and represents the compound having the structure:

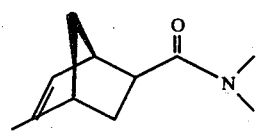

Figure 5:
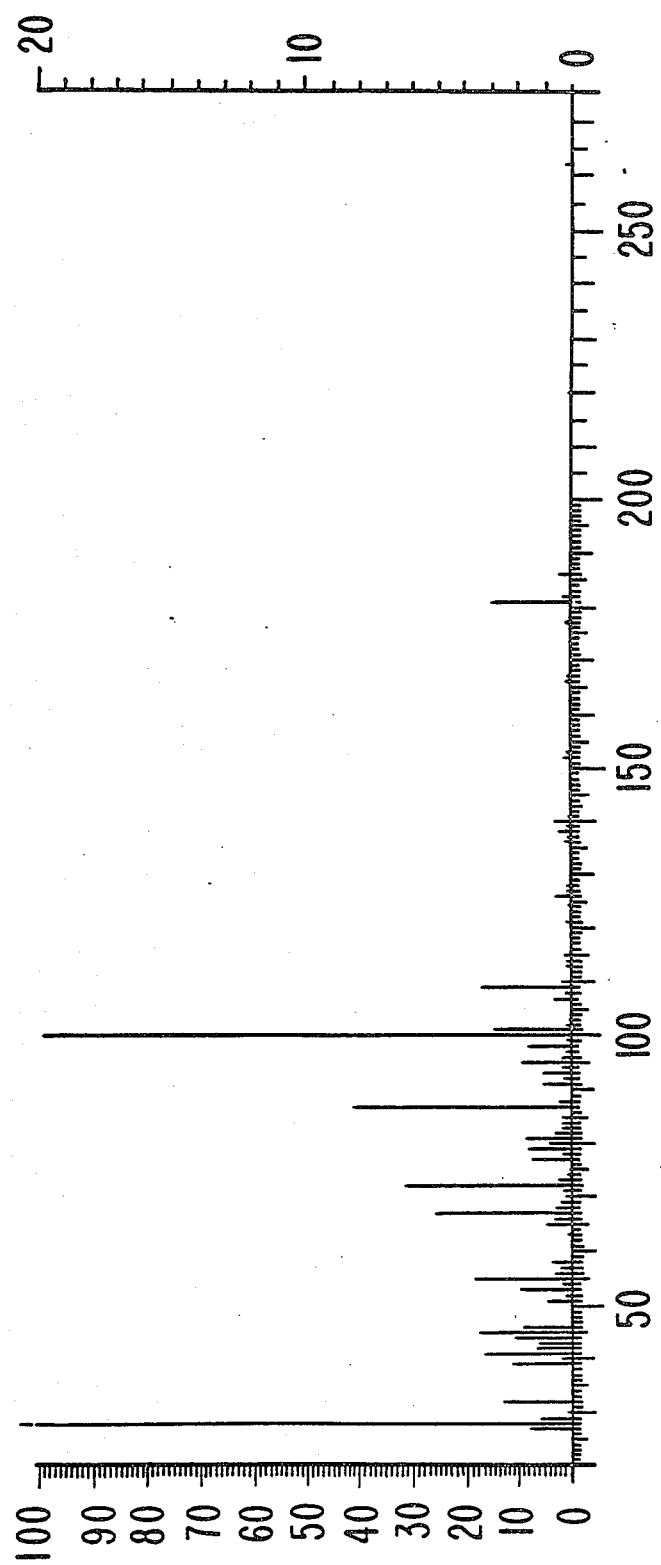

FIG. 5 represents the mass spectrum for the reaction produced according to Example III containing the compounds having the structures:

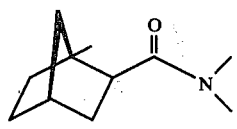

and

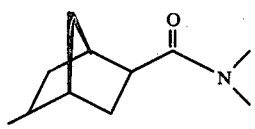

FIG. 6A represents the infra-red spectrum for fraction 1 of the distillation product of the reaction product of Example III which consists of the compound having the structure:

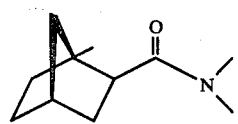

FIG. 6B represents the NMR spectrum for fraction 1 of the distillation product of the reaction product of Example III which consists of the compound having the structure:

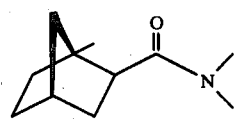

Figure 7A:
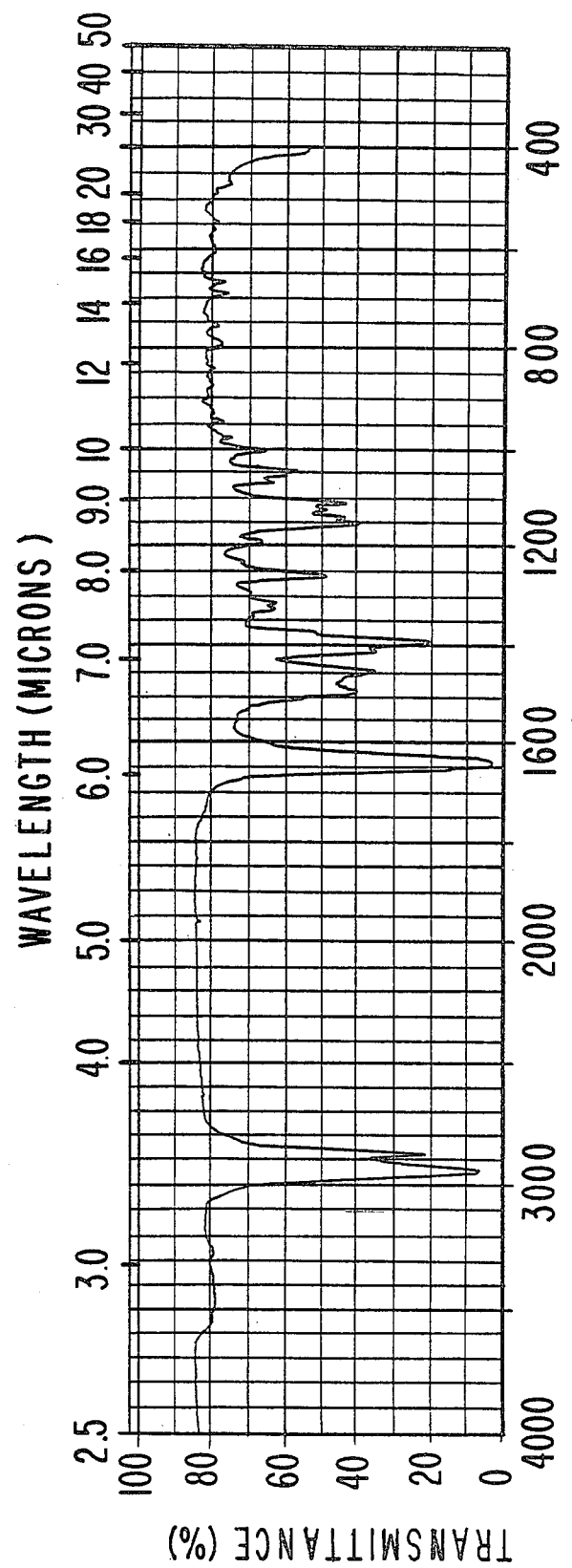

FIG. 7A represents the infra-red spectrum for fraction 8 of the distillation product of the reaction product of Example II which consists of the compound having the structure:

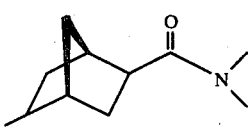

FIG. 7B represents the NMR spectrum for fraction 8 of the distillation product of the reaction product of Example II, which consists of the compound having the structure:

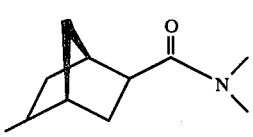

Figure 8:
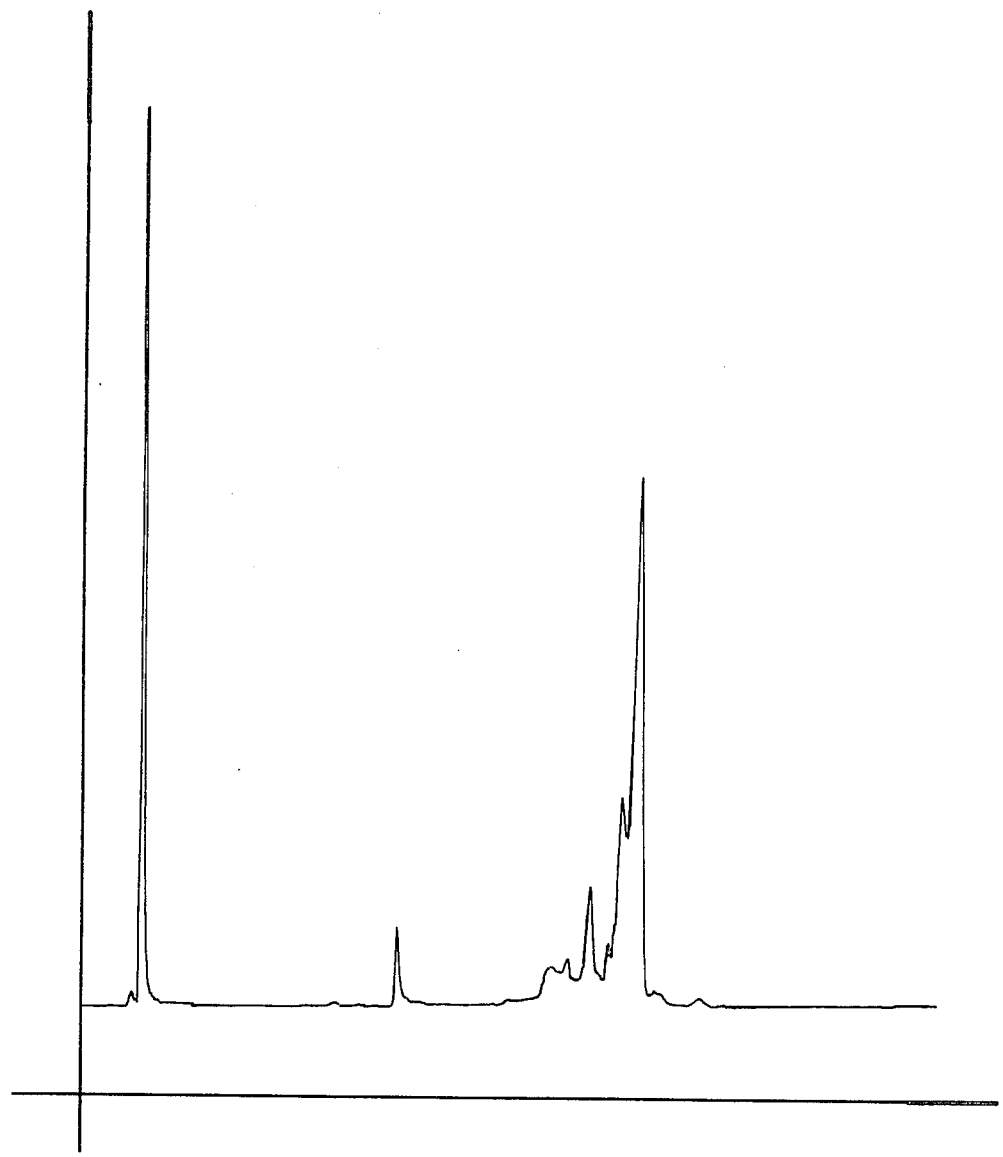

FIG. 8 is the GLC profile for the reaction product of Example XIX (conditions: Carbowax column programmed at 80°–220° C. at 8° C. per minute) containing the compound having the structure:

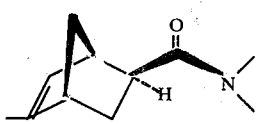

Figure 9:
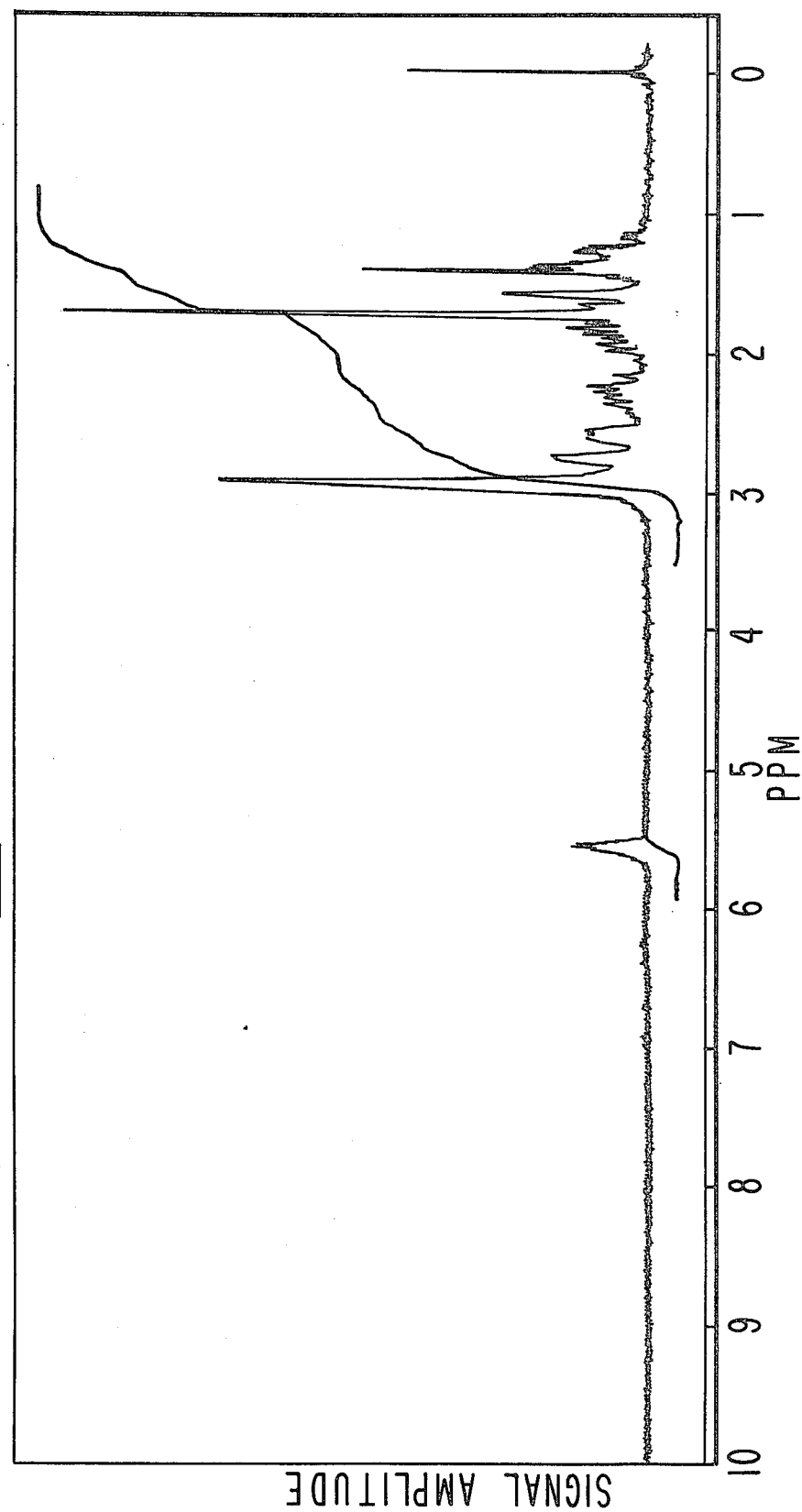

FIG. 9 is the NMR spectrum for the reaction product of Example XIX containing the compound having the structure:

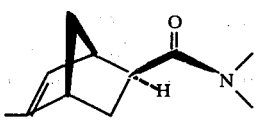

FIG. 10 is the infra-red spectrum for the reaction product of Example XIX containing the compound having the structure:

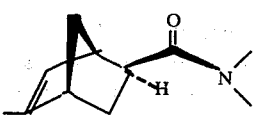

DETAILED DESCRIPTION OF FIG. 1

Figure 1:
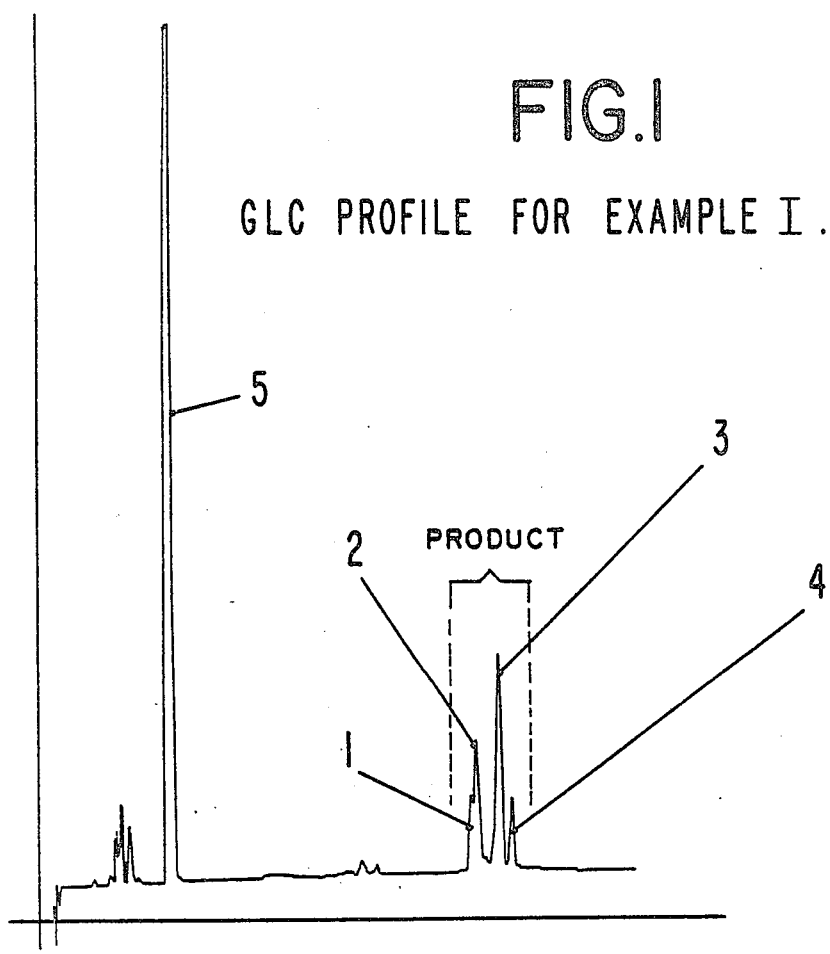
FIG. 1 represents the GLC profile for the reaction product of Example I, wherein peaks 1, 2, 3 and 4 represent peaks for compounds having the structures.

FIG. 1 represents the GLC profile for the reaction product of Example I. Peak 1 on said FIG. 1 represents the compound having the structure:

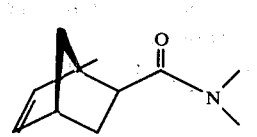

Peak 2 on FIG. 1 also represents the compound having the structure:

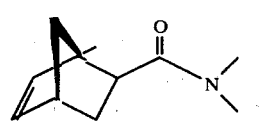

Peak 3 on said FIG. 1 represents the compound having the structure:

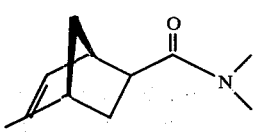

Peak 4 represents the compound having the structure:

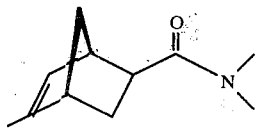

Peak 5 on said FIG. 1 represents the solvent peak on said GLC profile. The ratios of Peak 1: Peak 2: Peak 3: Peak 4: Peak 5 are:
14.76:
14.96:
15.77:
16.22:
3.90

THE INVENTION

It has now been discovered that novel solid and liquid perfume compositions, colognes and perfumed articles (e.g., solid or liquid anionic, cationic, nonionic or zwitterionic detergents, fabric softeners, dryer-added fabric softener articles, cosmetic powders and soaps) having intense and longlasting herbaceous, spearmint, spicy, powdery, floral, basil, caraway, fruity, castoreum-like and anise aromas and novel solid and liquid foodstuff, chewing gum, toothpaste, medicinal product, chewing tobacco, smoking tobacco and smoking tobacco article flavoring compositions, foodstuffs, toothpastes, chewing tobaccos, medicinal products, chewing gum, smoking tobaccos and smoking tobacco articles may be provided by the utilization of one or more of the substituted norbornane derivatives having the generic structure:

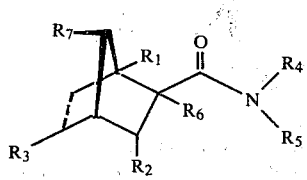

wherein the dashed line represents a carbon-carbon single bond or a carbon-carbon double bond and wherein $R_2$ is methyl or hydrogen; $R_6$ is methyl or hydrogen; $R_1$, $R_3$ or $R_7$ represent methyl or hydrogen, with the proviso that one of $R_1$, $R_3$ and $R_7$ represents methyl and the other two of $R_1$, $R_3$ and $R_7$ represent hydrogen; wherein $R_4$ and $R_5$ are the same or different and each represents hydrogen or $C_1-C_3$ lower alkyl in perfume compositions, perfumed articles, colognes, foodstuffs, chewing gums, toothpastes, medicinal products, chewing tobaccos, smoking tobaccos and smoking tobacco articles.

Unless otherwise specified, representations herein are intended to indicate "cis" isomers, "trans" isomers, mixtures of "cis" and "trans" isomers and "endo" isomers and "exo" isomers with respect to the norbornane ring moiety and dextro- and levorotatory isomers, as well as racemic mixtures of obstacle isomers of the norbornane derivatives of our invention.

Thus, the generic structure:

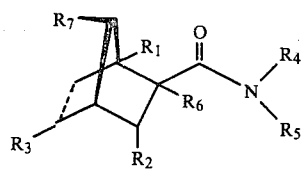

is intended to mean both "endo" and "exo" isomers having the structures:

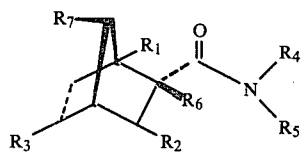

and

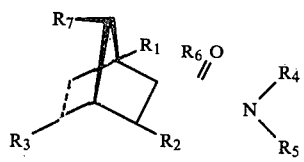

The novel substituted norbornane derivatives of our invention useful as indicated supra, may be produced by reacting a 1-methylcyclopentadiene or 2-methylcyclopentadiene having one of the structures:

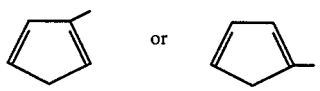

or a mixture of these methylcyclopentadienes defined according to the generic structure:

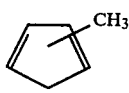

with an alkyl acrylamide derivative defined according to the generic structure:

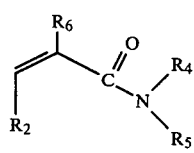

Generically, the methylcyclopentadiene derivative structures may be indicated by the generic structure:

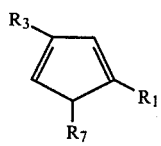

The substituted acrylamide structure represents a "cis" isomer or a "trans" isomer, or a mixture of "cis" and "trans" isomers. Thus, the "trans" isomer may be represented by the structure:

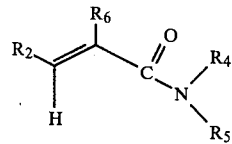

and the "cis" isomer may be represented by the structure:

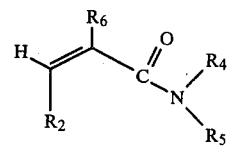

The Diels-Alder reaction may be carried out using a specific Lewis acid catalyst at low temperatures (e.g., 0°–50° C.) or in the absence of a catalyst, at elevated temperature (e.g., 170°–250° C.). Different isomers and proportions of isomers are produced depending on whether a catalytic reaction is carried out or a non-catalytic thermal Diels-Alder reaction is carried out as will be seen in the examples and subsequent paragraphs, infra.

Thus, when it is desired to carry out a "catalytic" Diels-Alder reaction, the catalyst for this reaction may be an alkyl aluminum dihalide or a dialkyl aluminum halide for example, RAlCl$_2$ or R$_2$AlCl wherein R represents methyl, ethyl or n-propyl or i-propyl. The preferred catalyst is ethyl aluminum dichloride. Other Lewis acids such as aluminum trichloride, stannic chloride, zinc chloride, ferric chloride and titanium tetrachloride have been attempted to be used but such attempts have proved to be unsuccessful with minimal or no yields in the product being produced. The temperature range of the reaction may vary from about 0° C. up to about 50° C. with ambient temperatures from 20° up to 30° C. being preferred. The reaction pressure will not affect the yield but, conveniently and economically, a reaction pressure of atmospheric is preferred. Thus, the catalyst for the reaction may be defined according to the formula:

$$R'_n AlCl_m$$

wherein R' is C$_1$–C$_3$ alkyl and the sum, m+n equals 3, with m being 1 or 2 and n being 1 or 2. The resulting reaction mass is a mixture of compounds containing unsaturation in the norbornane moiety defined according to the generic structure:

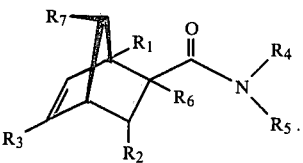

These compounds may be used "as is" for their organoleptic properties or the mixture of compounds may be further hydrogenated using hydrogen gas at supra-atmospheric pressures. When it is desired to use the compounds "as is", for their organoleptic properties, it is preferable to refine the reaction mass as by fractional distillation thereby creating a product usable as set forth above.

When the hydrogenation is carried out on a mixture of compounds containing compounds having the structure defined according to the genus:

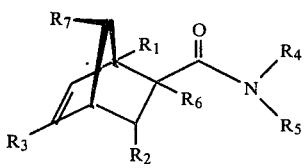

compounds containing the structures:

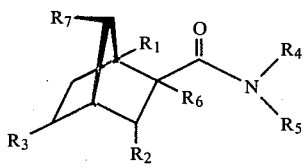

will be produced. It is preferable to carry out the hydrogenation at pressures of from about 20 psig up to about 2000 psig with a pressure range of from about 40 up to about 80 psig being preferred. It is also preferable for the reaction to be carried out in the presence of a catalyst such as Rainey nickel, Palladium-on-Carbon, Palladium-on-Calcium Carbonate, Palladium-on-Barium Sulfate, and Platinum. When using the Palladium-salt catalyst, it is preferred to use from about 3% up to about 12% Palladium-on salt, for example, 5% Palladium-on-Calcium Carbonate.

The reaction sequence including the catalytic Diels-Alder reaction which is embodied within our invention is generically set forth as follows:

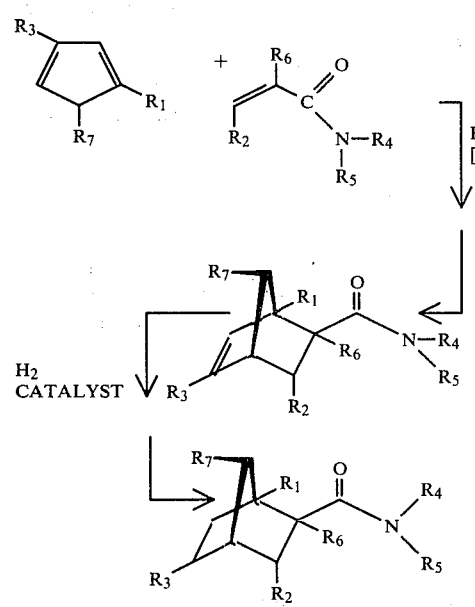

wherein $R_2$ is methyl or hydrogen; $R_6$ is methyl or hydrogen; $R_1$, $R_3$ or $R_7$ represent methyl or hydrogen, with the proviso that one of $R_1$, $R_3$ and $R_7$ represents methyl and the other two of $R_1$, $R_3$ and $R_7$ represent hydrogen; wherein $R_4$ and $R_5$ are the same or different and each represents hydrogen or $C_1$–$C_3$ lower alkyl.

When it is desired to carry out the thermal non-catalytic Diels-Alder reaction, the reaction takes place at temperatures of between 170° C. and 250° C. at elevated pressures in order to prevent the constituents of the reaction mass from evaporating. Too low a temperature of reaction will either give rise to inordinately long times of reaction, yields which are not commercially feasible since they are too low, or no reaction at all. However, temperatures above 250° C. are considered too high in that although the reaction is speeded up, the high temperature gives rise to an uncontrollable reaction and decomposition of reaction product which further gives rise to separation problems when attempting to obtain the substantially pure reaction product usable for its organoleptic properties. It has also been found that when carrying out the thermal reaction in certain instances this reaction is surprisingly, unexpectedly, unobviously and advantageously more specific than the low temperature catalytic Diels-Alder reaction. Thus, when reacting the methylcyclopentadiene dimer mixture with dimethylacrylamide according to the reaction sequence:

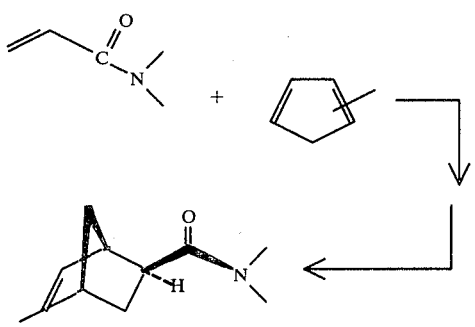

the reaction product having the structure:

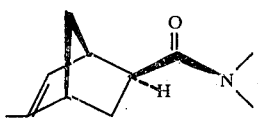

is produced without producing any other isomers thereof. This reaction product is the "endo" isomer of a specific isomeric product that would be expected to be one of many reaction products but that is, in fact, the only isomer produced.

Notwithstanding the foregoing statement, however, both the catalytic Diels-Alder reaction and the non-catalytic thermal Diels-Alder reaction, as a general rule, give rise to mixtures of isomers albeit different mixtures of isomers in different proportions.

When the norbornane derivative(s) of our invention are used as food flavor adjuvants or medicinal product flavor adjuvants or toothpaste flavor adjuvants or chewing gum flavor adjuvants, the nature of the co-ingredients included with each of said norbornane derivative(s) in formulating the product composition will also serve to augment or enhance the organoleptic characteristics of the ultimate foodstuff, chewing gum, medicinal product, toothpaste or chewing tobacco treated therewith.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma or taste nuances.

It is a further requirement that such material be organoleptically compatible with the foodstuff with which it is used so that the flavor and aroma nuances of such material taken together with the flavor and aroma nuances of the foodstuff (as a whole) give rise to a harmoniously aesthetically pleasing aroma and taste profile. Such materials, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials, lipids; carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as, palmitic acid, myristic acid and the like, mono- and diglycerides of fatty acids, lecithin, defoaming and flavor-dispersing agents such as sorbitan monostearate, potassium monostearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric, cur-cumin and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, 2-methyl-cis-3-pentenoic acid; ketones and aldehydes, e.g. octanal, n-decanal, acetaldehyde, acetophenone, acetone, acetyl methyl carbinol, acrolein, n-butanol, crotonal, diacetyl, 2-methyl butanal, beta, beta-dimethyl-acrolein, methyl-n-amyl ketone, n-hexenal, 2-hexenal, isopentanal, hydrocinnamic aldehyde, cis-3-hexenal, 2-heptenal, nonyl aldehyde, citral, 4-(p-hydroxyphenyl)-2-butanone, alphaionone, beta-ionone, 2-methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, $\beta$-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen1-ol, 3-methyl-3-buten-1-ol, 1-pentanol, 1-penten-3-ol, p-hydroxyphenyl-2-ethanol, isoamyl alcohol, fenchyl alcohol, isofenchyl alcohol, phenyl-2-ethanol, $\alpha$-terpineol, cis-terpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl $\alpha$-methyl-butyrate, ethyl propionate, ethyl salicylate, trans-2-hexenyl acetate, hexyl acetate, 2-hexenyl butyrate, hexyl butyrate, isoamyl acetate, isopropyl butyrate, dimethylanthranilate, methyl acetate, methyl butyrate, methyl caproate, methyl isobutyrate, $\alpha$-methylphenylglycidate, ethyl succinate, isobutyl cinnamate, cinnamyl formate, methyl cinnamate, and terpinyl acetate; hydrocarbons such as dimethyl naphthalene, dodecane, methyl diphenyl, methyl naphthalene, myrcene, cadinene, limonene, nephthalene, octadecane, tetradecane, tetramethyl naphthalene, tridecane, trimethyl naphthalene, undecane, caryophyllene, 1-phellandrene, p-cymene, 1-$\alpha$-pinene; pyrazines such as 2,3-dimethylpyrazine, 2,5-dimethylpyrazine, 2,6-dimethylpyrazine, 3-ethyl-2,5dimethylpyrazine, 2-ethyl-3,5,6-trimethylpyrazine, 3-isoamyl-2, 5-dimethyl-pyrazine, 5-isoamyl-2,3-dimethylpyrazine, 2-isoamyl3,5,6-trimethylpyrazine, isopropyl dimethylpyrazine, $\alpha$-methyl-3-ethylpyrazine, tetramethylpyrazine, trimethylpyrazine; essential oils, such as jasmine absolute, cassia oil, cinnamon bark oil, rose absolute, orris absolute, lemon essential oil, orange essential oil, grapefruit oil, Bulgarial rose, yara yara and vanilla; lactones such as gammanonalactone; sulfides, e.g., methyl sulfide and other materials such as maltol and acetals (e.g., 1,1-diethoxyethane, 1,1-dimethoxyethane and dimethoxyethane).

The specific flavoring adjuvants selected for use may be either solid or liquid depending upon the desired physical form of the ultimate product, i.e., foodstuff, whether simulated or natural, and should, in any event, (i) be organoleptically compatible with the norbornane derivative(s) of our invention by not covering or spoiling the organoleptic properties (aroma and/or taste) thereof; (ii) be non-reactive with the norbornane derivative(s) of our invention; and (iii) be capable of providing an environment in which the norbornane derivative(s) can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, augmented or enhanced. In contradistinction, in the preparation of solid products, e.g., simulated food-stuffs, ingredients capable of providing normally solid compositions should be selected such as various cellulose derivatives.

As will be appreciated by those skilled in the art, the amount of norbornane derivative(s) employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor and aroma. The primary requirement is that the amount selected be effective i.e., sufficient to augment or enhance the organoleptic characteristics of the parent composition, whether foodstuff per se, chewing gum per se, medicinal product per se, toothpaste per se, chewing tobacco per se, or flavoring composition.

The use of insufficient quantities of norbornane derivative(s) will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions, toothpaste compositions and chewing tobaccos compositions, it is found that quantities of norbornane derivative(s) ranging from a small but effective amount, e.g., 0.002 parts per million (ppm) up to about 50 parts per million (ppm) based on total composition are suitable. Concentrations in excess of the maximum quantity stated are not normally recommended, since they fail to provide commensurate enhancement of organoleptic properties. In those instances, where the norbornane derivative(s) is added to the foodstuff as an integral component of a flavoring composition, it is, of course, essential that the total quantity of flavoring composition employed be sufficient to yield an effective norbornane derivative (s) concentration in the foodstuff product.

Food flavoring compositions prepared in accordance with the present invention preferably contain the norbornane derivative(s) in concentrations ranging from about 0.005% up to about 5% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornane derivative(s) of our invention with, for example, gum arabic, gum tragacanth, carrageenan and the like, and thereafter spray-drying the resultant mixture whereby to obtain the particulate solid product. Pre-prepared flavor mixes in powder form, e.g., fruit-flavored powder mixes are obtained by mixing the dried solid components, e.g., starch, sugar and the like and the norbornane derivative(s) in a dry blender until the requisite degree of uniformity is achieved.

It is presently preferred to combine with the norbornane derivative(s) of our invention, the following adjuvants:

Bergamot oil;
Citral;
Amyl alcohol;
Ethyl acetate;
5 phenyl-4-pentenal;
5 phenyl-2-pentenal;
n-Octanal;
n-Decanal;
Limonene;
Geraniol;
Cadinene;
Dimethylanthranilate;
Vanillin;
Amyl butyrate;
2-(n-pentyl)-thiazole;
2-(i-butyl)-thiazole;
2-(i-propyl)-thiazole;
2-(n-propyl)-thiazole;
The dimethyl acetal of 2-phenyl-4-pentenal;
Methional;
4-Methylthiobutanal;
2-Ethyl-3-acetyl pyrazine;
Tetramethyl pyrazine;
2-Methyl pyrazine;
2-Trans hexenal;
Maltol;
2-Phenyl-4-penetenal;
2-Phenyl-4-penetenal dimethyl acetal; and
2-Phenyl-4-penetenal diethyl acetal.

The norbornane derivative(s) and one or more auxiliary perfume ingredients, including, for example, hydrocarbons, alcohols, ketones, aldehydes, nitriles, esters, lactones or cyclic esters, synthetic essential oils and natural essential oils, may be admixed so that the combined odors of the individual components produce a pleasant and desired fragrance, particularly and preferably in herbaceous, spearmint, spicy, powdery, floral, basil, caraway, fruity, castoreum-like and anise fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh-smelling materials.

In perfume compositions, it is the individual components which contribute to their particular olfactory characteristics, however, the overall sensory effect of the perfume composition will be at least the sum total of the effects of each of the ingredients. Thus, one or more of the norbornane derivative(s) of our invention can be used to alter, modify or enhance the aroma characteristics of a perfume composition, for example, by utilizing or moderating the olfactory reaction contributed by another ingredient in the composition.

The amount of norbornane derivative(s) of our invention which will be effective in perfume compositions as well as perfumed articles and colognes depends on many factors, including the other ingredients, their amounts and the effects which are desired. It has been found that perfume compositions containing as little as 0.01% of norbornane derivative(s) or even less (e.g., 0.005%) can be used to impart a herbaceous, spearmint, spicy, powdery, floral, basil, caraway, fruity, castoreum-like and anise aroma to soaps, detergents (including anionic, nonionic, cationic and zwitterionic solid or liquid detergents), cosmetics, fabric softeners, dryer-added fabric softener articles, fabric whiteners, optical brightener compositions, hair preparations and other products. The amount employed can range up to 70% of the fragrance components and will depend on considerations of cost, nature of the end product, the effect desired on the finished product and the particular fragrance sought.

The norbornane derivative(s) of our invention are useful (taken alone or together with other ingredients in perfume compositions) in detergents and soaps, space odorants and deodorants, perfumes, colognes, toilet water, bath preparations such as lacquers, brilliantines, pomades and shampoos; cosmetic preparations, such as creams, deodorants, hand lotions and sun screens; powders such as talcs, dusting powders, face powders and the like. As little as 0.005% of the norbornane derivative(s) (in the ultimate perfumed article) will suffice to impart an intense herbaceous, spearmint, spicy, powdery, floral, basil, caraway, fruity, castoreum-like and anise fragrance to various types of perfumed articles. Generally no more than 3% of the norbornane derivatives based on the ultimate end product (perfumed article) is required.

In addition, the perfume composition or fragrance composition of our invention can contain a vehicle, or carrier for the norbornane derivative(s). The vehicle can be a liquid such as a non-toxic alcohol, a non-toxic glycol, or the like. The carrier can also be an absorbent solid, such as a gum (e.g., gum arabic), or components for encapsulating the composition (such as gelatin).

An addition aspect of our invention provides an organoleptically improved smoking tobacco product and additives therefor, as well as methods of making the same which overcome problems heretofore encountered in which desired sweet, fruity flavor characteristics and aroma characteristics of natural tobacco (prior to smoking and on smoking in the main stream and in the side stream) are created or enhanced or modified or augmented and may be readily controlled and maintained at the desired uniform level regardless of variations in the tobacco components of the blend.

This invention further provides improved tobacco additives and methods whereby various natural aromatic tobacco flavoring characteristics with sweet and fruity notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more norbornane derivatives of our invention.

In addition to the norbornane derivatives of our invention, other flavoring and aroma additives may be added to the smoking tobacco material or substitute therefor either separately or in mixture with the norbornane derivatives as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b-)-furan
4-Hydroxyhexanoic acid, gamma lactone; and
Polyisoprenoid hydrocarbons defined in Example V of U.S. Pat. No. 3,589,372, issued on June 29, 1971.

II. Natural Oils

Celery seed oil;
Coffee extract;
Bergamot oil;
Cocoa extract;
Nutmeg oil; and
Origanum oil.

An aroma and flavoring concentrate containing one or more norbornane derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as enhancement or the imparting of sweet and/or fruity notes, we have found that satisfactory results are obtained if the proportion by weight of the sum total of norbornane derivative(s) to smoking tobacco material is between 50 ppm and 1,500 ppm (0.015%–0.15%). We have further found that satisfactory results are obtained if the proportions by weight of the sum total of norbornane derivative used to flavoring material is between 1,500 and 15,000 ppm (0.15%–1.5%).

Any convenient method for incorporating the norbornane derivative(s) into the tobacco product may be employed. Thus, the norbornane derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the norbornane derivative(s) taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed.

In such cases, the tobacco treated by the norbornane derivative(s) have in excess of the amounts or concentrations above indicated so that when blended with other tobaccos, the final product will have the percentage within the indicated range.

In accordance with one specific example of our invention an aged, cured and shredded domestic burley tobacco is sprayed with a 20% ethanol solution of the compound having the structure:

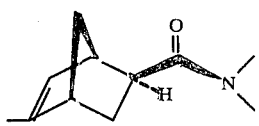

in an amount of mixture to provide tobacco composition containing 800 ppm by weight of the mixture of the amide on a dry basis. Thereafter the alcohol is removed by evaporation and the tobacco is manufactured into cigarettes by the usual techniques. The cigarette when treated as indicated has a desired and pleasing aroma which is detectable in the main stream and the side stream when the cigarette is smoked. This aroma is described as being sweeter, fruity, more aromatic, more tobacco-like having sweet, fruity notes.

While our invention is particularly useful in the manufacture of smoking tobacco such as cigarette tobacco, cigar tobacco and pipe tobacco, other tobacco products formed from sheeted tobacco dust or fines may also be used. Likewise, the norbornane derivative(s) of our invention can be incorporated with materials such as filter tip materials (e.g., cellulose acetate filters wherein sweet, fruity effects are desired), seam paste, packaging materials and the like which are used along with tobacco to form a product adapted for smoking. Furthermore, the norbornane derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

It will thus be apparent that the norbornane derivative(s) of our invention can be utilized to alter, modify or enhance sensory properties, particularly organoleptic properties such as fragrances of a variety of consumable materials including perfume compositions, perfumed articles and colognes and such as aromas and tastes of a variety of consumable materials including smoking tobacco compositions, smoking tobacco articles, foodstuffs, chewing gums, toothpastes, chewing tobaccos and medicinal products.

The following examples serve to illustrate processes for specifically producing the norbornane derivative(s) useful in our invention.

The following examples also serve to illustrate specific embodiments of our invention.

It will be understood that these examples are illustrative and the invention is to be considered to be restricted thereto only as indicated in the appended claims.

All parts and percentages given herein are by weight unless otherwise specified.

EXAMPLE I

PREPARATION OF 1- AND 5-METHYL-5-NORBORNENE-2-CARBOXYLIC ACID AMIDES (CATALYTIC DIELS-ALDER REACTION)

Reaction:

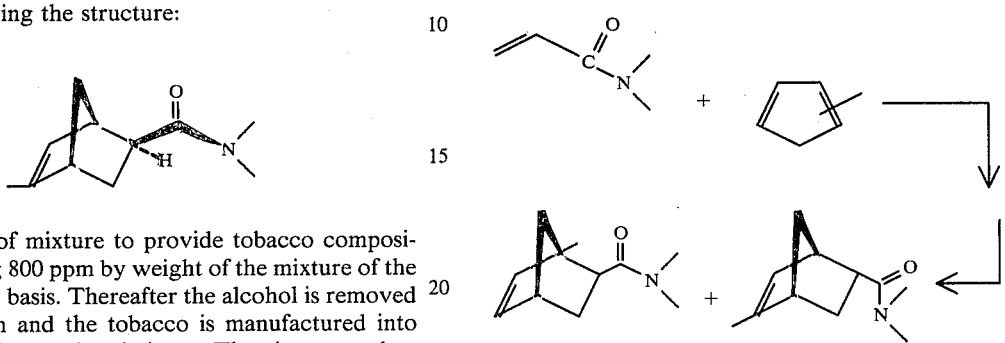

Into a 1 liter reaction flask, equipped with thermometer, stirrer, condenser, addition funnel, cooling bath and nitrogen purge are placed 200 grams of M, N-dimethyl acrylamide and 300 ml. toluene. While maintaining the reaction at temperature at 20°–25° C., over a period of twenty minutes, 50 grams of 25% ethyl aluminum dichloride is added dropwise to the reaction mass. After the addition of the ethyl aluminum dichloride is complete, over a period of twenty-five minutes while maintaining the reaction temperature at 20°–25° C., 325 grams of a 50% solution of methyl cyclopentadiene in toluene is added to the reaction mass dropwise. After the addition of the methyl cyclopentadiene solution, the reaction mass is then quenched by pouring same into 500 ml. of a 10% sodium chloride solution. The aqueous phase and the organic phase are separated, and the aqueous phase is extracted with one 200 ml portion of toluene. The organic phases are combined and washed with two 500 ml portions of 10% sodium chloride solution. The solvent is then stripped off of the organic phase and the reaction mass is distilled yielding the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 48/35 | 110/110 | 2.0 | 9:1 | 12 |
| 2 | 75 | 123 | 1.0 | 9:1 | 20.3 |
| 3 | 78 | 129 | 1.0 | 9:1 | 24.3 |
| 4 | 79 | 129 | 1.0 | 9:1 | 22 |
| 5 | 84 | 129 | 1.0 | 9:1 | 29.3 |
| 6 | 84 | 129 | 1.0 | 9:1 | 29.5 |
| 7 | 85 | 130 | 1.0 | 9:1 | 27.5 |
| 8 | 85 | 131 | 1.0 | 9:1 | 27.5 |
| 9 | 85 | 132 | 1.0 | 9:1 | 26 |
| 10 | 85 | 134 | 1.0 | 9:1 | 29.4 |
| 11 | 87 | 179 | 1.0 | 9:1 | 13.5 |
| 12 | 83 | 240 | 1.0 | 9:1 | 4.5 | after adding to the reaction mixture 9 grams of Primol ®, 0.5 grams of Ionox ® and 5 grams of calcium carbonate.

The resulting reaction product contains compounds having the structures:

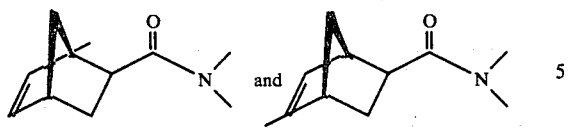

as confirmed by NMR mass spectral and IR analyses.

FIG. 1 represents the GLC profile for the reaction product of Example I, wherein peaks 1,2,3 and 4 represent peaks for compounds having the structures:

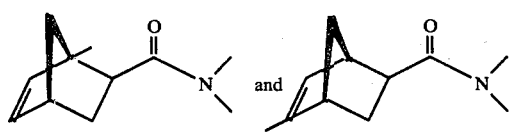

FIG. 2 represents the mass spectrum for the reaction product for the reaction product of Example I which contains the compounds having the structures:

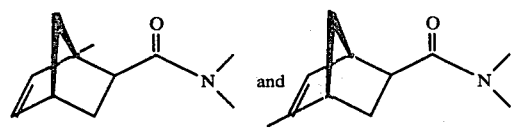

FIG. 3A represents the NMR spectrum for peak 1 of the GLC profile of the reaction product of Example I which represents the compound having the structure:

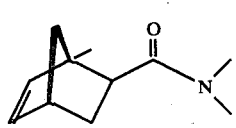

FIG. 3B represents the NMR spectrum for peak 2 of the GLC profile of the reaction product of Example I which represents the compound having the structure

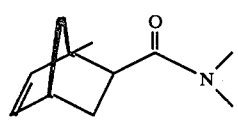

FIG. 3C represents the NMR spectrum for peak 3 of the GLC profile of the reaction product of Example I and represents the compound having the structure:

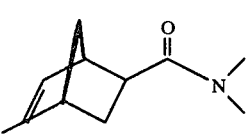

FIG. 3D represents the NMR spectrum for peak 4 of the GlC profile of the reaction product of Example I and represents the compound having the structure:

FIG. 4A represents the infra-red spectrum for peak 1 of the GLC profile of the reaction product of Example I which represents the compound having the structure:

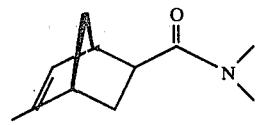

FIG. 4B represents the infra-red spectrum for peak 2 of the GLC profile of the reaction product of Example I and represents the compound having the structure:

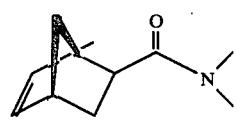

FIG. 4C represents the infra-red spectrum for peak 3 of the GLC profile of the reaction product of Example I and represents the compound having the structure:

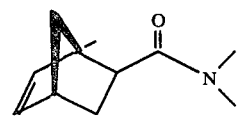

FIG. 4D represents the infra-red spectrum for peak 4 of the GLC profile of the reaction product of Example I and represents the compound having the structure:

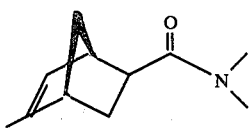

EXAMPLE II

The following minty, floral and herbal type formula are prepared:

| Ingredient | Parts by Weight |
|---|---|
| Geranium Bourbon | 20.0 |
| Rosemary Oil Spanish | 10.0 |
| Lavender Oil Barreme | 10.0 |
| Thyme Oil White | 10.0 |
| Amyl Cinnamic Aldehyde | 10.0 |
| Sauge Sclaree French | 5.0 |
| Sandalwood Oil | 5.0 |
| Galbanum Oil | 5.0 |
| Patchouli Oil Light | 5.0 |
| Cedarwood Oil Light | 15.0 |
| Product produced according to Example I, bulked frac- | 45.0 |

| Ingredient | Parts by Weight |
|---|---|
| -continued | |
| tions 1–8 containing and consisting of the compounds having the structures: 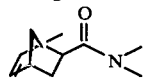 and 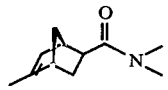 | |

When the composition of matter prepared according to Example I is incorporated into the formula at 45.0%, the composition of matter has added to it a pleasant, herbaceous, spearmint, spicy, powdery, floral, basis, caraway and anise aroma to the already spicy, herbal and floral type formulation.

EXAMPLE III

PREPARATION OF 1- and 5-METHYL-5-NORBORNANE-2-CARBOXYLIC ACID AMIDES

Reaction:

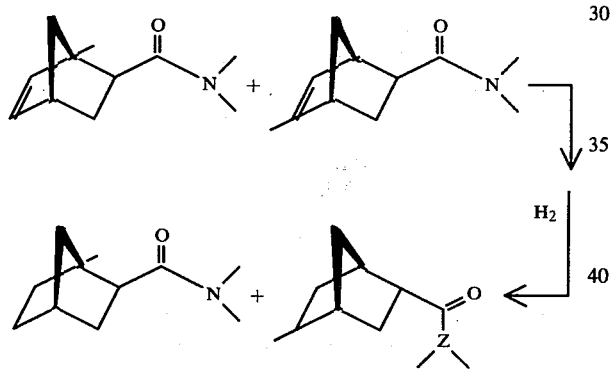

Into a 500 ml. pressure bottle equipped with Parr shaker is placed 200 grams of the reaction product of Example I containing the compounds having the structures:

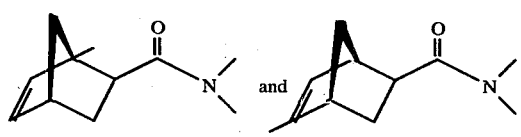

4 grams of Rainey nickel and 50 ml. of isopropyl alcohol. The reaction mixture is pressurized to 50 psig after the pressure bottle is closed and the reaction mass is purged five times with hydrogen in order to remove any air. Over a period of nine hours, while maintaining the reaction pressure at 25–50 psig, hydrogen gas is added to the reaction mass (total up-take 91 psig hydrogen).

At the end of the reaction, the pressure bottle is opened and the catalyst is filtered and the solvent is stripped off. The reaction product is then distilled on a 12 inch Silver Mirror Goodloe column yielding the following fractions:

| Fraction No. | Vapor Temp. (°C.) | Liquid Temp. (°C.) | mm/Hg Pressure | Reflux Ratio | Weight of Fraction (g.) |
|---|---|---|---|---|---|
| 1 | 63/66 | 111/111 | 0.8/0.8 | 9:1 | 19.7 |
| 2 | 65 | 111 | 0.6 | 9:1 | 21.5 |
| 3 | 80 | 111 | 1.0 | 9:1 | 24.8 |
| 4 | 85 | 111 | 1.0 | 9:1 | 22.1 |
| 5 | 85 | 111 | 1.0 | 9:1 | 20.1 |
| 6 | 85 | 111 | 1.0 | 9:1 | 26.6 |
| 7 | 85 | 119 | 1.0 | 9:1 | 29.4 |
| 8 | 84 | 210 | 1.0 | 9:1 | 8.8 |

NMR, IR and mass spectral analysis yield the information that the resulting product contains the compounds having the structures:

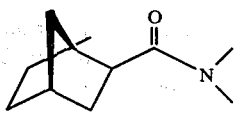

and

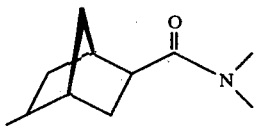

The distillation as set forth above is carried out with 6 grams of Primol ® and 0.5 grams of Ionox ®.

FIG. 5 is the mass spectrum for the reaction product produced according to this example containing the compounds having the structures:

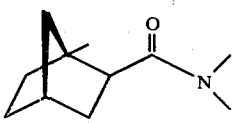

and

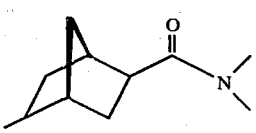

Bulked fractions 3–8 have a peppery, herbaceous, spearmint, caraway aroma with basil and aniseed undertones.

FIG. 6A represents the infra-red spectrum for fraction 1 of the distillation product of the reaction product of Example III which consists of the compound having the structure:

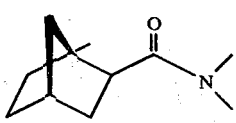

FIG. 6B represents the NMR spectrum for fraction 1 of the distillation product of the reaction product of Example III which consists of the compound having the structure:

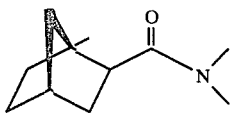

FIG. 7A represents the infra-red spectrum for fraction 8 of the distillation of the reaction product of Example II, which consists of the compound having the structure:

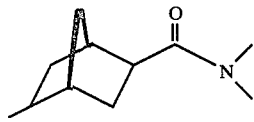

FIG. 7B represents the NMR spectrum for fraction 8 of the distillation product of the reaction product of Example II, which consists of the compound having the structure:

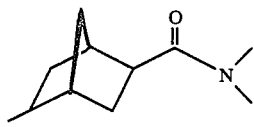

EXAMPLE IV

The following minty, floral and herbal type formula are prepared:

| Ingredient | Parts by Weight |
|---|---|
| Geranium Bourbon | 20.0 |
| Rosemary Oil Spanish | 10.0 |
| Lavender Oil Barreme | 10.0 |
| Thyme Oil White | 10.0 |
| Amyl Cinnamic Aldehyde | 10.0 |
| Sauge Sclaree French | 5.0 |
| Sandalwood Oil | 5.0 |
| Galbanum Oil | 5.0 |
| Patchouli Oil Light | 5.0 |
| Cedarwood Oil Light | 15.0 |
| Product produced according to Example III, bulked fractions 3-8 containing and consisting of the compounds having the structures: | |

(structures shown)

and (structures shown)

When the composition of matter prepared according to Example III is incorporated into the formula at 45.0%, the composition of matter has added to it a pleasant, peppery, herbaceous, spearmint, caraway aroma with basil and aniseed undertones to this already spicy, herbal and floral type formulation.

EXAMPLE V

A stable lotion is prepared with the following formulations:

| Ingredients | Parts by Weight |
|---|---|
| Poly(N,N-dimethyl-3,5-dimethylene piperidinium chloride) (Merquat 100, Merck & Co., U.S.A., average molecular weight 50,000-100,000, viscosity in 40% aqueous solution, 10,000 cps. | 1.0 |
| Cocoamidopropyl dimethyl glycine (betaine) | 5.7 |
| Myristyl dimethylamine oxide | 12.0 |
| Stearic monoethanolamide opacifier | 2.0 |
| Perfume material as indicated in Table I (below) giving rise to the aroma profiles as indicated in Table I (below) | 0.5 |
| Water, colour, salts, U.V. absorber | q.s. to 100 |

Two or three bottle capfuls of the above lotion held under the tap releasing the water into the bathtub yields a copiously foamed bubble bath with no visible precipitation flocculation, or "bathtub ring" even using hard water. Bathing in this bath is found to have a cleansing and pleasing emollient effect on the skin as described above.

When, after immersion in this bath, the body is soaped, rinsed and dried, an even better, more lasting emollient moisturizing effect on the skin is observed. The foam or bubbles are substantially unaffected by the soaping step, and no precipitate, flocculate or "bathtub ring", or any bothersome film or coating on the bathtub surface is found.

The aroma produced is as set forth in Table I below:

TABLE I

| Product | Aroma Profile |
|---|---|
| Product produced according to Example I, bulked fractions 1-8 consisting of compounds having the structures: (structures) | Herbaceous, spearmint, spicy, powdery and anise aroma |
| Perfume composition prepared according to Example II | A minty, spicy, herbal and floral aroma increasing in intensity on dry-out |
| Product produced according to Example III, bulked fractions 3-8, consisting of the compounds having the structures: (structures) | Peppery, herbaceous, spearmint, caraway aroma with basil and aniseed undertones |
| Perfume compositions prepared according to Example IV | A minty, spicy, herbal and floral aroma increasing in intensity |

TABLE I-continued

| Product | Aroma Profile |
|---|---|
| | on dry-out |

EXAMPLE VI

The following formulation is prepared with results and properties and use similar to those described in Example III.

| Ingredients | Parts by Weight |
|---|---|
| "Merquat 100" | 1.0 |
| Cocoamidopropyl dimethyl glycine | 8.0 |
| Myristyl dimethyl amine oxide | 16.0 |
| Perfume ingredient as set forth in Table II (below) giving rise to the aroma profiles as set forth in Table II (below) | 0.8 |
| Water | q.s. to 100 |

The composition is a clear liquid. Its viscosity may be increased by addition of a lauric or myristic diethanolamide or a soluble polyethylene glycol ester such as polyethylene glycol 6000. In addition, this composition may be rendered opaque by addition of stearic monoethanolamide stearate, polyethylene glycol 600 monostearate or a glyco amido stearate such as "Cerasynt 1P".

TABLE II

| Product | Aroma Profile |
|---|---|
| Product produced according Example I, bulked fractions 1-8 consisting of compounds having the structures: 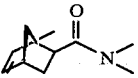 and 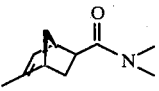 | Herbaceous, spearmint, spicy, powdery and anise aroma |
| Perfume composition prepared according to Example II | A minty, spicy, herbal and floral aroma increasing in intensity on dry-out |
| Product produced according to Example III, bulked fractions 3-8, consisting of the compounds having the structures: 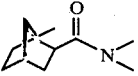 and 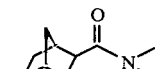 | Peppery, herbaceous, spearmint, caraway aroma with basil and aniseed undertones |
| Perfume compositions prepared according to Example IV | A minty, spicy, herbal and floral aroma increasing in intensity on dry-out |

EXAMPLE VII

The following shampoo is prepared containing the following ingredients:

| Ingredients | Parts by Weight |
|---|---|
| Tridecyloxy polyethoxy ethanol of ten ethoxy groups | 17.3 |
| Polyoxyethylene (20) sorbitan monolaurate | 7.5 |
| Myristyl dimethylamine oxide (30% active) | 25.0 |
| $C_{10}$-$C_{20}$ fatty acyl monoethanolamide (cocomonoethanolamide) | 2.5 |
| Polyacrylamide of molecular weight of about 1,500,000 | 0.2 |
| Hydrogen peroxide (30% aqueous solution) | 0.5 |
| Perfume ingredient as indicated at Table III (below) giving rise to the aroma profiles as indicated in Table III (below) | 1.0 |
| Deionized water (3 micromhos/cm conductivity | 46.0 |

A shampoo of the above composition is made in the following manner. First, the tridecyloxy polyethoxy ethanol is added to a clean mixing tank, with the agitator on, and the amine oxide, polyoxyethylene sorbitan monolaurate and cocomonoethanolamine are added sequentially, with continued agitation. The mix is then heated to 68° C., until the cocomonoethanolamide is melted and/or dissolved. The hydrogen peroxide solution is then admixed with the mentioned nonionics and mixing is continued for about half an hour, in which the peroxide destroys any free amines or other harmful impurities that may be present. The mix is then cooled to 38° C.

In a separate mixer the polyacrylamide is gradually added to the formula weight of deionized water, with the mixer on. Addition is effected carefully and slowly (the polyacrylamide is sprinkled in) to avoid the production of "fish eyes" in the mix. After dissolving of the polyacrylamide the solution thereof is added to the first mixing tank with agitation and is blended with the nonionics, such mixings being at room temperature. Subsequently, the perfume as indicated in Table III (below) giving rise to the aroma profile as set forth in Table III (below) is admixed with the balance of the composition and mixing is continued for another half hour.

TABLE III

| Product | Aroma Profile |
|---|---|
| Product produced according Example I, bulked fractions 1-8 consisting of compounds having the structures: 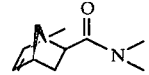 and  | Herbaceous, spearmint, spicy, powdery and anise aroma |
| Perfume composition prepared according to Example II | A minty, spicy, herbal and floral aroma increasing in intensity on dry-out |
| Product produced according to Example III, bulked fractions 3-8, consisting of the compounds having the structures: 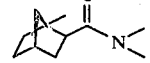 | Peppery, herbaceous, spearmint, caraway aroma with basil and aniseed undertones |

TABLE III-continued

| Product | Aroma Profile |
|---|---|
| and 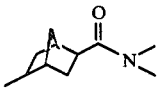 Perfume compositions prepared according to Example IV | A minty, spicy, herbal and floral aroma increasing in intensity on dry-out |

The product made is an excellent shampoo of satisfactory viscosity and aroma, foaming power, foam stability, low conductivity and good shampooing effects. The viscosity is about 1,000 centipoises at 20° C. and the conductivity, using the Hach Conductivity Meter, is 750 micromhos/cm. The foaming power is 250 ml. and the foam stability is 22 seconds, by the test method previously described. In comparison, a commercial shampoo based on triethanolamine lauryl sulphate detergent has a conductivity of about 22,000 micromhos/cm, a viscosity of about 1,500 centipoises, a foaming power of about 380 ml. and a foam stability of 60 seconds.

In panel evaluations of the experimental shampoo compared to a different commercial product, in actual shampooing, the experimental formula was adjudged significantly better in being less drying, producing a softer feel for the wet hair, leaving the wet hair easier to comb, being less prone to accumulate static charges (less flyaway) and having a foam of better appearance and feel. Additionally, the experimental product was judged better in almost all hair effect properties, with the control only being about equal to it in curl retention. In properties other than those mentioned, the experimental product was better in rinsability, the control was better in foam build-up rate and the foams were about equal in volume and stability.

In the shampooing described herein and in subsequent Examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE VIII

Fabric Freshener Composition

A fabric fastener composition is prepared as follows:

| Ingredients | Parts by Weight |
|---|---|
| Sodium bicarbonate | 3 |
| "Kyro" EOB (Trademark)* | 1 |
| Perfume ingredient as set forth in Table IV (below) giving rise to an aroma as set forth in Table IV (below) | 1 |
| Water | 0.05 |

The composition of this Example is prepared by simply mixing the ingredients.

The above described composition is applied to a lightly soiled and wrinkled fabric as droplets (ca. 5.0 mm avg. size) using a trigger action sprayer having a nozzle which is adjustable to provide composition droplets in the desired range. The composition is applied at a rate of about 1 gram of composition to about 10 grams of fabric.

The fabric is then placed in an automatic dryer and dried, with tumbling action, at a temperature of 60° C.-80° C. for a period of 15 minutes. The fabric is rendered free of wrinkles and static, and has a fresh appearance and pleasant odor profile as set forth in Table IV below.

In the foregoing procedure, substantially the same results were obtained when sodium carbonate is substituted for the sodium bicarbonate.

TABLE IV

| Product | Aroma Profile |
|---|---|
| Product produced according Example I, bulked fractions 1-8 consisting of compounds having the structures: 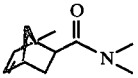 and 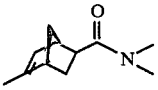 Perfume composition prepared according to Example II | Herbaceous, spearmint, spicy, powdery and anise aroma<br><br>A minty, spicy, herbal and floral aroma increasing in intensity on dry-out |
| Product produced according to Example III, bulked fractions 3-8, consisting of the compounds having the structures: 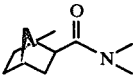 and  Perfume compositions prepared according to Example IV | Peppery, herbaceous, spearmint, caraway aroma with basil and aniseed undertones<br><br>A minty, spicy, herbal and floral aroma increasing in intensity on dry-out |

EXAMPLE IX

Perfumed Liquid Detergent

Concentrated liquid detergents (lysine salts of n-dodecyl benzene sulfonic acid as more specifically described in U.S. Pat. No. 3,948,818, issued on Apr. 6, 1976) with aromas as indicated in Table V below are prepared containing 0.10%, 0.15%, 0.20%, 0.25%, 0.30%, 0.40%, 0.50% and 0.80% of the perfume ingredient as set forth in Table V below. The detergents are prepared by adding and homogeneously mixing the appropriate quantity of perfume ingredient as set forth in Table V below. The detergents all possess aromas as set forth in Table V below with the intensity of each increasing with greater concentrations of the perfume ingredient as indicated in Table V below.

TABLE V

| Product | Aroma Profile |
|---|---|
| Product produced according Example I, bulked fractions 1-8 consisting of compounds | Herbaceous, spearmint, spicy, powdery and anise aroma |

TABLE V-continued

| Product | Aroma Profile |
|---|---|
| having the structures: 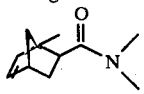 and 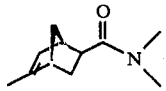 | |
| Perfume composition prepared according to Example II | A minty, spicy, herbal and floral aroma increasing in intensity on dry-out |
| Product produced according to Example III, bulked fractions 3–8, consisting of the compounds having the structures: 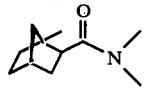 and 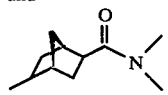 | Peppery, herbaceous, spearmint, caraway aroma with basil and aniseed undertones |
| Perfume compositions prepared according to Example IV | A minty, spicy, herbal and floral aroma increasing in intensity on dry-out |

EXAMPLE X

Preparation of a Cologne and Handkerchief Perfume

The perfume ingredient as set forth in Table VI below is incorporated into colognes at concentrations of 2.0%, 2.5%, 3.0%, 3.5%, 4.0%, 5.0% and 6.0% in 75%, 80%, 90% and 95% aqueous ethanol solutions. Distinct and definite aromas as set forth in Table VI below are imparted to the colognes. The perfume ingredients as indicated in Table VI below are also added to handkerchief perfumes at concentrations of 15%, 20%, 25%, 30% and 35% (in 75%, 80%, 90% and 95% aqueous ethanol) and aroma profiles as set forth in Table VI are imparted to the handkerchief perfume.

TABLE VI

| Product | Aroma Profile |
|---|---|
| Product produced according Example I, bulked fractions 1–8 consisting of compounds having the structures: 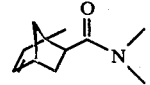 and 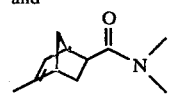 | Herbaceous, spearmint, spicy, powdery and anise aroma |
| Perfume composition prepared according to Example II | A minty, spicy, herbal and floral aroma increasing in intensity on dry-out |
| Product produced according to Example III, bulked fractions 3–8, consisting of the compounds | Peppery, herbaceous, spearmint, caraway aroma with basil and |

TABLE VI-continued

| Product | Aroma Profile |
|---|---|
| having the structures: 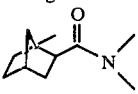 and 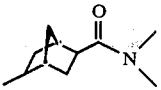 | aniseed undertones |
| Perfume compositions prepared according to Example IV | A minty, spicy, herbal and floral aroma increasing in intensity on dry-out |

EXAMPLE XI

Grapefruit Formulation

The following formulation is prepared:

| Ingredients | Parts by Weight |
|---|---|
| Grapefruit oil | 88 |
| Nootkatone | 4 |
| Bergamot oil | 2 |
| Citral | 3 |
| Amyl alcohol | 1 |
| Ethyl acetate | 1 |
| 5-Phenyl-4-pentenal | 1 |
| N,N-1, (and 5)-Trimethyl-5-norbornane 2-carboxamide, prepared according to Ex. III (bulked fractions 3–8) | 0.5 |

When the above grapefruit formulation is added to water at the rate of 1%, an excellent grapefruit drink is prepared. The N,N-1(and 5)-Trimethyl-5-norbornane 2-carboxamide prepared according to Example II (bulked fractions 3–8) gives an intense sweet, anise note to the instant formulation, thereby rendering it more desirable. Additional quantities of the N,N-1 (and 5)-Trimethy-5-norbornane 2-carboxamides prepared according to Example III, (e.g., one additional part by weight) can replace the nootkatone in the grapefruit formulation.

The foregoing grapefruit formulation can also be enhanced by one or more of the following materials at one part by weight:
- 4-Mercapto-5-nonanone (prepared according to U.S. Pat. No. 4,064,278)
- 4-Mercapto-5-nonanol (prepared according to U.S. Pat. No. 4,064,278)
- 3-Mercapto-2,6-dimethyl-4-heptanone (prepared according to U.S. Pat. No. 4,064,278)
- 2-Mercapto-3-pentanone (prepared according to U.S. Pat. No. 4,064,278)
- 3-Mercapto-4-heptanol (prepared according to U.S. Pat. No. 4,064,278)

Thus, our invention is also intended to cover the mixtures of alpha-oxy (oxo) Mercaptans and N,N-1 (and 5)-Trimethyl-5-norbornane 2-carboxamides and the corresponding unsaturated norbornane derivative(s) in ratios of 0.01 parts by weight alpha-oxy (oxo) Mercaptan: 1 part by weight norbornane derivative(s) up to 0.01 parts by weight norbornane derivative(s): 1 part by weight alpha-oxy (oxo) Mercaptan of U.S. Pat. No. 4,064,278.

EXAMPLE XII

A. Powder Flavor Composition 20 grams of the flavor composition of Example XI containing the compounds having the structures:

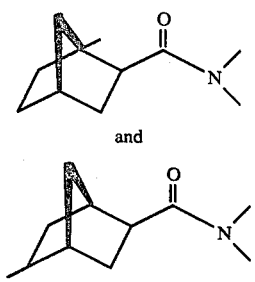

and prepared according to Example II (bulked fractions 3 and 8) is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel spread of 50,000 rpm.

B. Sustained Release Flavor

The following mixture is prepared:

| Ingredients | Parts by Weight |
|---|---|
| Liquid Grapefruit Flavor of Example XI | 20 |
| Propylene Glycol | 9 |
| Cab-O-Sil ® M-5 (Brand of Silica produced by the Cabot Corporation of 125 High Street Boston, Mass. 02112 Physical Properties: Surface area: 200 m$^2$/gm Nominal particle size: 0.012 microns Density: 2.3 lbs/cu. ft.) | 5.00 |

The Cab-O-sil is dispersed in the liquid grapefruit flavor composition of Example XI with vigorous stirring, thereby resulting in a viscous liquid. 71 parts by weight of the powder flavor composition of Part A, supra, is then blended into the said viscous liquid, with stirring at 25%C. for a period of thirty minutes, thereby resulting in a dry, free-flowing sustained release grapefruit flavor powder.

EXAMPLE XIII 10 parts by weight of 5 -Bloom pigskin gelatin is added to 90 parts by weight of water at a temperature of 150° F. The mixture is agitated until the gelatin is completely dissolved and the solution is cooled to 120° F. 20 parts by weight of the liquid grapefruit flavor composition of Example XI is added to the solution which is then homogenized to form an emulsion having particle size typically in the range of 2-5 microns. This material is kept at 120° F. under which conditions the gelatin will not gel.

Coacervation is induced by adding, slowly and uniformly, 40 parts by weight of a 20% aqueous solution of sodium sulphate. During coacervation, the gelatin molecules are deposited uniformly about each oil droplet as a nucleus.

Gelatin is effected by pouring the heated coacervate mixture into 1,000 parts by weight of 7% aqueous solution of sodium sulphate at 65° F. The resulting gelled coacervate may be filtered and washed with water at temperatures below the melting point of gelatin, to remove the salt.

EXAMPLE XIV

Chewing Gum

100 Parts by weight of chicle are mixed with 4 parts by weight of the flavor prepared in accordance with Example XII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting grapefruit flavor.

EXAMPLE XV

Chewing Gum 100 parts by weight of chicle are mixed with 18 parts by weight of the flavor prepared in accordance with Example XIII. 300 parts of sucrose and 100 parts of corn syrup are added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting grapefruit flavor.

EXAMPLE XVI

Toothpaste Formulation

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example XII |
| 100.00 (Total) | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.

4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure yields a pleasant grapefruit flavor, of constant strong intensity throughout said procedure (1–1.5 minutes).

EXAMPLE XVII

Chewable Vitamin Tablets

The flavor material produced according to the process of Example XII is added to a Chewable Vitamin Tablet Formulation at the rate of 10 grams/kilogram which chewable vitamin tablet formulation is prepared as follows:

In a Hobart Mixer the following materials are blended to homogeneity:

| | Gms/1000 tablets |
|---|---|
| Vitamin C (ascorbic acid) as ascorbic acid-sodium ascorbate mixture 1:1 | 70.00 |
| Vitamin B₁ (thiamine mononitrate) as Rocoat ® thiamine mononitrate 33⅓% (Hoffman La Roche) | 4.0 |
| Vitamin B₂ (riboflavin) as Rocoat ® riboflavin 33⅓% | 5.0 |
| Vitamin B (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B₁₂ (cyanocobalamin) as Merck 0.1% in gelatin | 3.5 |
| Vitamin E (dl-alpha tocopheryl acetate) as dry vitamin E acetate 33⅓% Roche | 6.6 |
| d-biotin | 0.004 |
| Flavor of Example XII | (as indicated above) |
| Certified lake color | 5.0 |
| Sweetener - sodium saccharin | 1.0 |
| Magnesium stearate lubricant | 10.0 |
| Mannitol q.s. to make | 500.00 |

Preliminary tablets are prepared by sluggish with flat-faced punches and grinding the slugs to 14 mesh. 13.5 g Dry Vitamin A acetate and 0.6 g Vitamin D are then added as beadlets. The entire blend is then compressed using concave punches at 0.5 g each.

Chewing of the resultant tablets yields a pleasant, long-lasting, consistently strong grapefruit flavor for a period of 12 minutes.

EXAMPLE XVIII

Chewing Tobacco

Onto 100 pounds of tobacco for chewing (85% Wisconsin leaf and 15% Pennsylvania leaf) the following the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XII | 0.4 |

The resultant product is redried to a moisture content of 20%. On chewing, this tobacco has an excellent substantially consistent, long lasting, licorice/grapefruit flavor profile in conjunction with the tobacco note.

EXAMPLE XIX

Preparation of N,N,5-Trimethyl-5-Norbornene-Endo-2-Carboxamide

Reaction:

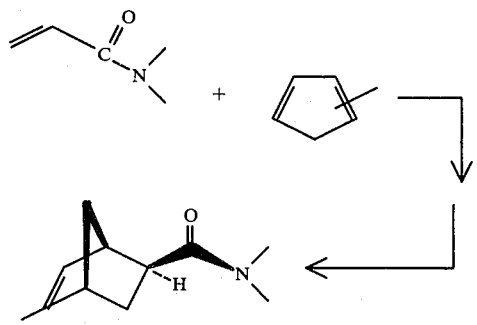

Into a 1000 cc autoclave equipped for pressure reactions, is placed 104 grams of methylcyclopentadiene dimer and 250 grams of N,N-dimethyl acrylamide. The autoclave is closed and placed in a Parr shaker. The contents of the autoclave are heated to 200° C. while maintaining the pressure at 125–145 psig and with shaking maintained at that temperature and pressure for a period of 7 hours.

At the end of the 7 hour period, the contents of the autoclave are cooled and the autoclave is opened. The reaction mass is then removed from the autoclave and distilled using a micro distillation apparatus yielding the following fractions:

| Fraction Number | Vapor Temp. °C. | Liquid Temp. °C. | Head Vac. mm. Hg. | Weight of Fraction |
|---|---|---|---|---|
| 1 | 70/73 | 100/100 | .6/.6 | 13.6 |
| 2 | 76 | 101 | .6 | 12.3 |
| 3 | 78 | 114 | .6 | 17 |
| 4 | 86 | 121 | .6 | 17.9 |
| 5 | 91 | 124 | .6 | 13 |
| 6 | 104 | 141 | .8 | 18.1 |
| 7 | 99 | 142 | .6 | 10.8 |
| 8 | 99 | 149 | .6 | 14.7 |
| 9 | 99 | 184 | .6 | 10.2 |
| 10 | 104 | 216 | .6 | 6.2 |

The GLC profile prior to distillation is set forth in FIG. 8. The GLC conditions are: Carbowax column programmed at 80°–220° C. at 8° C. per minute. NMR and IR analysis confirm that the product produced has the structure:

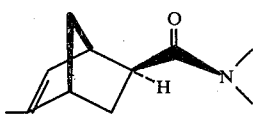

FIG. 9 is the NMR spectrum for the compound having the structure:

FIG. 10 is the infra-red spectrum for the compound having the structure:

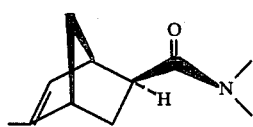

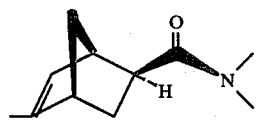

The resulting compound has an excellent fruity aroma with a castoreum-like undertone. The material tested for its organoleptic properties results from the bulking of fractions 3-8 of the foregoing distillation.

EXAMPLE XX

Tobacco Formulation

A tobacco mixture is produced by admixing the following ingredients:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco. The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 0.1% to all of the cigarettes produced using the above tobacco formulation. Half of the cigarettes are then treated with 500 to 1,500 ppm of the N,N-1(and 5)-trimethyl-5-norbornene-2-carboxamide mixture produced according to Example I.

The control cigarettes not containing the norbornyl derivative and the experimental cigarettes which contain the norbornyl derivative are evaluated by paired comparison and the results are as follows:

The experimental cigarettes are found, on smoking, to have a sweeter, fruity, more natural tobacco-like aroma prior to smoking and on smoking in the main stream and the side stream. The experimental cigarettes containing the product produced according to Example I are basically more burley tobacco-like.

All cigarettes are evaluated for smoke flavor with a 20 mm cellulose acetate filter.

EXAMPLE XXI

The following minty, floral and herbal type formula is prepared:

| Ingredient | Parts by Weight |
| --- | --- |
| Geranium Bourbon | 20.0 |
| Rosemary Oil Spanish | 10.0 |
| Lavender Oil Barreme | 10.0 |
| Thyme Oil White | 10.0 |
| Amyl Cinnamic Aldehyde | 10.0 |
| Sauge Sclaree French | 5.0 |
| Sandalwood Oil | 5.0 |
| Galbanum Oil | 5.0 |
| Patchouli Oil Light | 5.0 |
| Cedarwood Oil Light | 15.0 |
| Product produced according to Example XIX, bulked fractions 3-8 containing and consisting of the compound having the structure: 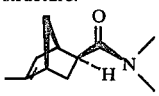 | 45.0 |

When the composition of matter prepared according to Example XIX is incorporated into the formula at 45.0%, the composition of matter has added to it a pleasant fruity, castoreum-like, herbaceous, spearmint, spicy, powdery, floral, basis, caraway and anise aroma to the already spicy, herbal and floral type formulation.

EXAMPLE XXII

Preparation of a Cologne and Handkerchief Perfume

The perfurme ingredient as set forth in Table VII below is incorporated into colognes at concentrations of 2.0%, 2.5%, 3.0%, 3.5%, 4.0%, 5.0% and 6.0% in 75%, 80%, 90% and 95% aqueous ethanol solutions. Distinct and definitive aromas as set forth in Table VII below are imparted to the colognes. The perfume ingredients as indicated in Table VII below are also added to handkerchief perfumes at concentrations of 15%, 20%, 25%, 30% and 35% (in 75%, 80%, 90% and 95% aqueous ethanol) and aroma profiles as set forth in Table VII below are imparted to the handkerchief perfume:

TABLE VII

| Product | Aroma Profile |
| --- | --- |
| Product produced according to Example XIX, bulked fractions 3-8 consisting of the compound having the structure: | A fruity, castoreum-like, herbaceous, spearmint, spicy, powdery and anise aroma. |
| Perfume composition prepared according to Example XXII | A minty, spicy, herbal and floral aroma with important fruity and castoreum-like nuances increasing in intensity on dry-out. |

EXAMPLE XXIII

Perfumed Liquid Detergent

Concentrated liquid detergents (lysine salt of n-dodecyl benzene sulfonic acid as more specifically described in U.S. Pat. No. 3,948,818, issued on Apr. 6, 1976) with aromas as indicated in Table VIII below are prepared containing 0.10%, 0.15%, 0.20%, 0.25%, 0.30%, 0.40%, 0.50% and 0.80% of the perfume ingredient as set forth in Table VIII below. The detergents are prepared by adding and homogeneously mixing the appropriate quantity of perfume ingredient as set forth in Table VIII below. The detergents all possess aromas as set forth in Table VIII below with the intensity of each increasing with greater concentrations of the perfume ingredient as indicated in Table VIII below.

TABLE VIII

| Product | Aroma Profile |
| --- | --- |
| Product produced according to Example XIX, bulked fractions 3-8 consisting of the compound having the structure: 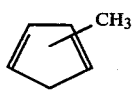 | A fruity, castoreum-like, herbaceous, spearmint, spicy, powdery and anise aroma. |
| Perfume composition prepared according to Example XXII | A minty, spicy, herbal and floral aroma with important fruity and castoreum-like nuances increasing in intensity on dry-out. |

What is claimed is:

1. A product containing a major proportion of isomers defined according to the structures:

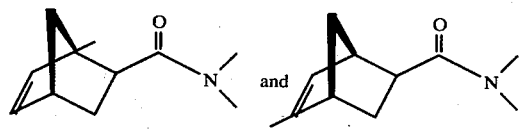

produced according to the process of reacting methyl cyclopentadiene having the structure:

with N,N-dimethyl acrylamide in the presence of a catalyst defined according to the formula:

R'$_n$AlCl$_m$ wherein R' is $C_1$-$C_3$ alkyl and the sum, m+n=3 with m being 1 or 2 and n being 1 or 2 at a temperature in the range of from about 0° C. up to about 50° C.

2. A product containing a major proportion of compounds defined according to the structures:

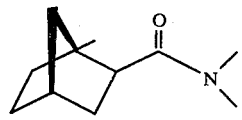

produced according to the process of:

(a) Reacting N,N-dimethyl acrylamide with methyl cyclopentadiene having the structure:

in the presence of a catalyst defined according to the formula:

R'$_n$AlCl$_m$ wherein R' is $C_1$-$C_3$ alkyl and the sum, m+n=3 with m being 1 or 2 and n being 1 or 2 at a temperature in the range of from about 0° C. up to about 50° C. whereby a mixture of isomers containing a major proportion of compounds defined according to the structures:

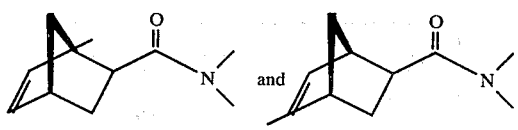

are formed and then (b) Hydrogenating the resulting reaction product at pressures of from about 20 psig up to about 2,000 psig in the presence of a catalyst selected from the group consisting of Raney Nickel, palladium on carbon, palladium on calcium carbonate, palladium on barium sulfate and platinum.

* * * * *